United States Patent
Binch et al.

(10) Patent No.: US 8,372,835 B2
(45) Date of Patent: Feb. 12, 2013

(54) PYRROLOPYRAZINES AND PYRAZOLOPYRAZINES USEFUL AS INHIBITORS OF PROTEIN KINASES

(75) Inventors: Hayley Binch, Harwell (GB); Daniel Robinson, Abingdon (GB); Damien Fraysse, Abingdon (GB); Andrew Miller, Upton (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 12/847,136

(22) Filed: Jul. 30, 2010

(65) Prior Publication Data

US 2011/0081364 A1 Apr. 7, 2011

Related U.S. Application Data

(62) Division of application No. 11/285,497, filed on Nov. 22, 2005, now Pat. No. 7,795,259.

(60) Provisional application No. 60/630,115, filed on Nov. 22, 2004.

(51) Int. Cl.
*A01N 43/58* (2006.01)
*A01N 43/60* (2006.01)
*A61K 31/50* (2006.01)
*A61K 31/495* (2006.01)

(52) U.S. Cl. .................................................. 514/249

(58) Field of Classification Search ........................ None
See application file for complete search history.

(56) References Cited

FOREIGN PATENT DOCUMENTS

| WO | 03/000588 | 1/2003 |
|---|---|---|
| WO | 03/024969 | 3/2003 |
| WO | 2004/041162 | 5/2004 |
| WO | 2005/028475 | 9/2005 |
| WO | 2005/084249 | 9/2005 |
| WO | 2005/085248 | 9/2005 |
| WO | 2006/015124 | 2/2006 |

OTHER PUBLICATIONS

Dorwald F.A. Side Reactions in Organic Synthesis, 2004, Wiley: VCH, Weinheim p. IX of Preface.
Abdel-Magid, Ahmed F.; Encyclopedia of Reagents for Organic Synthesis, Online Posting Date: Apr. 15, 2001, last accessed Jun. 19, 2009.
Voss, Jungen; Encyclopedia of Reagents for Organic Synthesis, Article Online Posting Date: Sep. 15, 2006, last accessed Jun. 19, 2009.
Meier, et al.; Encyclopedia of Reagents for Organic Synthesis, Article Online Posting Date: Mar. 14, 2008, last accessed Jun. 19, 2009.

*Primary Examiner* — Jeffrey Murray
(74) *Attorney, Agent, or Firm* — Rory C. Stewart

(57) ABSTRACT

The present invention relates to compounds useful as inhibitors of Aurora protein kinase. The invention also provides pharmaceutically acceptable compositions comprising said compounds and methods of using the compositions in the treatment of various disease, conditions, or disorders. The invention also provides processes for preparing compounds of the inventions.

2 Claims, No Drawings

PYRROLOPYRAZINES AND PYRAZOLOPYRAZINES USEFUL AS INHIBITORS OF PROTEIN KINASES

CROSS-REFERENCE TO RELATED APPLICATIONS

The present invention is a divisional application of U.S. patent application Ser. No. 11/285,497 filed Nov. 22, 2005 now U.S. Pat. No. 7,795,259, which claims the benefit, under 34 U.S.C. §119, to U.S. Provisional Application No. 60/630,115 filed on Nov. 22, 2004; the entire disclosure of which is incorporated herein by reference.

TECHNICAL FIELD OF THE INVENTION

The present invention is in the field of medicinal chemistry and relates to compounds that are protein kinase inhibitors, compositions containing such compounds and methods of use. More particularly, the compounds are inhibitors of Aurora kinases and are useful for treating disease states, such as cancer, that are alleviated by Aurora kinase inhibitors.

BACKGROUND OF THE INVENTION

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are attractive and proven targets for new therapeutic agents to treat a range if human diseases, with examples including Gleevec and Tarceva.

The Aurora kinases are especially attractive due to their association with numerous human cancers and the role they play in promoting proliferation of these cancer cells. (Harrington et al., Nature Med., 2004, 10, 262)

The Aurora proteins are a family of three highly related serine/threonine kinases (termed Aurora-A, -B and -C) that are essential for progression through the mitotic phase of cell cycle. Specifically Aurora-A plays a crucial role in centrosome maturation and segregation, formation of the mitotic spindle and faithful segregation of chromosomes. Aurora-B is a chromosomal passenger protein that plays a central role in regulating the alignment of chromosomes on the meta-phase plate, the spindle assembly checkpoint and for the correct completion of cytokinesis.

Overexpression of Aurora-A, -B or -C has been observed in a range of human cancers including colorectal, ovarian, gastric and invasive duct adenocarcinomas. In addition amplification of the AURKA locus that encodes for Aurora-A correlates with poor prognosis for patients with node-negative breast cancer. Furthermore overexpression of Aurora-A has been shown to transform mammalian fibroblasts, giving rise to aneuploid cells containing multipolar spindles.

A number of studies have now demonstrated that depletion or inhibition of Aurora-A or -B in human cancer cell lines by siRNA, dominant negative or neutralising antibodies disrupts progression through mitosis with accumulation of cells with 4N DNA, and in some cases this is followed by endoreduplication and cell death.

SUMMARY OF THE INVENTION

It has now been found that compounds of this invention, and pharmaceutically acceptable compositions thereof, are effective as inhibitors of protein kinases. In certain embodiments, these compounds are effective as inhibitors of Aurora protein kinases, and in some embodiments, as inhibitors of Aurora A protein kinase. These compounds have the general formula I:

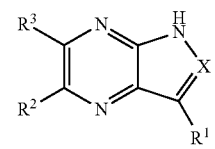

I or a pharmaceutically acceptable salt thereof, wherein X, $R^1$, $R^2$ and $R^3$ are as defined below.

These compounds and pharmaceutical compositions thereof are useful for treating or preventing a variety of disorders, including, but not limited to, heart disease, diabetes, Alzheimer's disease, immunodeficiency disorders, inflammatory diseases, hypertension, allergic diseases, autoimmune diseases, destructive bone disorders such as osteoporosis, proliferative or hyperproliferative disorders, infectious diseases, immunologically-mediated diseases, and viral diseases.

The compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation. The compositions are especially useful for disorders such as chronic myelogenous leukemia (CML), acute myeloid leukemia (AML), acute promyelocytic leukemia (APL), rheumatoid arthritis, asthma, osteoarthritis, ischemia, cancer (including, but not limited to, ovarian cancer, breast cancer and endometrial cancer), liver disease including hepatic ischemia, heart disease such as myocardial infarction and congestive heart failure, pathologic immune conditions involving T cell activation, and neurodegenerative disorders.

The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

1. General Description of Compounds of the Invention

The present invention relates to a compound of formula I:

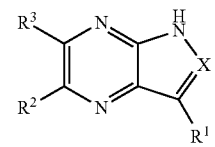

I or a pharmaceutically acceptable salt thereof,
wherein X is CH or N;
$R^1$ is $C_{6-10}$ aryl or 5-14 membered heteroaryl independently and optionally substituted with up to five J groups;
$R^2$ and $R^3$ are each independently hydrogen, halogen, —CN, —NO₂, —V—R, —V—$R^a$, or —V—$R^b$ optionally substituted with $R^7$;
$R^4$ is $R^5$, —$C_{1-4}$aralkyl, —$COR^5$, —$CO_2R^5$, —$CON(R^5)_2$, —$SO_2R^5$, or —$SO_2N(R^5)_2$; or two $R^4$ taken together with the atom(s) to which they are attached form an optionally substituted 3-10 membered cycloaliphatic or 5-14 membered heterocyclyl;

$R^5$ is optionally substituted R, $C_{6-10}$ aryl, $C_{3-10}$ cycloaliphatic, 5-14 membered heteroaryl, or 5-14 membered heterocyclyl; or two $R^5$ groups, together with the atom(s) to which they are attached, form an optionally substituted 3-7 membered monocyclic or 8-14 membered bicyclic ring;

R is H or optionally substituted $C_{1-6}$ aliphatic;

$R^a$ is optionally substituted $C_{6-10}$ aryl, $C_{3-10}$ cycloaliphatic, 5-14 membered heteroaryl, or 5-14 membered heterocyclyl;

$R^b$ is —$OR^5$, —$N(R^5)_2$, or —$SR^5$;

V is a bond, Q, or an optionally substituted $C_{1-6}$ aliphatic chain, wherein up to two methylene units of the chain are optionally and independently replaced by Q in a chemically stable arrangement;

Q is —$NR^5$—, —S—, —O—, —CS—, —C(O)O—, —OC(O)—, —C(O)—, —C(O)C(O)—, —C(O)$NR^5$—, —$NR^5$C(O)—, —$NR^5$C(O)O—, —$SO_2NR^5$—, —$NR^5SO_2$—, —C(O)$NR^5NR^5$—, —$NR^5$C(O)$NR^5$—, —OC(O)$NR^5$, —$NR^5NR^5$—, —$NR^5SO_2NR^5$—, —SO—, —$SO_2$—, —PO—, —$PO_2$—, or —$PONR^5$—;

each J is independently halogen, optionally substituted $C_{1-6}$aliphatic, $C_{1-6}$alkoxy, —$N(R^5)_2$, —$C(O)R^5$, —NC(O)$R^5$, —$C(O)NR^5$, —$C(O)OR^5$, $SOR^5$, —$SO_2R^5$, or —U—$(R^6)_n$ wherein each $R^6$ is independently H or optionally substituted $C_{1-12}$ aliphatic, $C_{3-10}$ cycloaliphatic, $C_{7-12}$benzofused cycloaliphatic, $C_{6-10}$aryl, 5-14 membered heterocyclyl, 5-14 membered heteroaryl, —$OR^5$, —$N(R^4)_2$, or —$SR^5$;

U is a bond or optionally substituted $C_{1-6}$ aliphatic wherein up to two methylene units are optionally and independently replaced by Y in a chemically stable arrangement;

Y is a group selected from —O—, —$NR^5$—, —S—, —$NR^5C(O)$—, —$N(SO_2)$—, —$NR^5C(O)NR^5$—, —$C(O)NR^5$—, —C(O)—, —OC(O)$NR^5$—, —$NR^5C(O)O$—, —C(O)O—, or —OC(O)—;

n is 1 or 2;

$R^7$ is =O, =NR, =S, —CN, —$NO_2$, or —Z—$R^c$;

Z is a bond or optionally substituted $C_{1-6}$ aliphatic wherein up to two methylene units of the chain are optionally and independently replaced by —$NR^5$—, —S—, —O—, —CS—, —C(O)O—, —OC(O)—, —C(O)—, —C(O)C(O)—, —$C(O)NR^5$—, —$NR^5C(O)$—, —$NR^5C(O)O$—, —$SO_2NR^5$—, —$NR^5SO_2$—, —$C(O)NR^5NR^5$—, —$NR^5C(O)NR^5$—, —OC(O)$NR^5$—, —$NR^5NR^5$—, —$NR^5SO_2NR^5$—, —SO—, —$SO_2$—, —PO—, —$PO_2$—, or —$POR^5$—;

$R^c$ is an optionally substituted 3-8-membered saturated, partially unsaturated, or fully unsaturated monocyclic ring having 0-3 heteroatoms independently selected from nitrogen, oxygen, or sulfur, or an optionally substituted 8-12 membered saturated, partially unsaturated, or fully unsaturated bicyclic ring system having 0-5 heteroatoms independently selected from nitrogen, oxygen, or sulfur;

In certain embodiments, for compounds described directly above:

a) when $R^1$ is unsubstituted phenyl, $R^2$ and $R^3$ are each independently not H, $CH_3$, or unsubstituted phenyl;
b) when $R^1$ is unsubstituted phenyl, $R^2$ is not CN and $R^3$ is not $NH_2$;
c) when X is N, and $R^2$ and $R^3$ are H, $R^1$ is not unsubstituted 2-naphthyl;
d) when one of $R^2$ or $R^3$ is optionally substituted phenyl, the other one of $R^2$ or $R^3$ is not

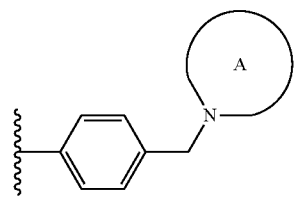

wherein ring A is an optionally substituted heterocyclyl.

In other embodiments a) $R^1$ is not

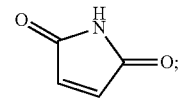

b) when $R^1$ is a five-membered heteroaryl, it is not substituted in the ortho position with J wherein J is a 2,3-dihalo substituted phenyl.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members. Suitable heterocycles include 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow. The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Suitable heteroaryl rings include 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

An aryl (including aralkyl, aralkoxy, aryloxyalkyl and the like) or heteroaryl (including heteroaralkyl and heteroarylalkoxy and the like) group may contain one or more substituents and thus may be "optionally substituted". Unless otherwise defined above and herein, suitable substituents on the unsaturated carbon atom of an aryl or heteroaryl group are generally selected from halogen; —R°; —OR°; —SR°; phenyl (Ph) optionally substituted with R°; —O(Ph) optionally substituted with R°; —(CH$_2$)$_{1-2}$(Ph), optionally substituted with R°; —CH=CH(Ph), optionally substituted with R°; a 5-6 membered heteroaryl or heterocyclic ring optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N(R°)$_2$; —OC(O)N(R°)$_2$; —OC(O)R°; —C(O)N(OR°)R°; —C(NOR°)R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(=NH)—N(R°)$_2$; —P(O)$_2$R°; —PO(R°)$_2$; —OPO(R°)$_2$; or —(CH$_2$)$_{0-2}$NHC(O)R°; wherein each independent occurrence of R° is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R°, on the same substituent or different substituents, taken together with the atom(s) to which each R° group is bound, to form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group of $R^o$ are selected from $NH_2$, $NH(C_{1-4}aliphatic)$, $N(C_{1-4}aliphatic)_2$, halogen, $C_{1-4}aliphatic$, OH, $O(C_{1-4}aliphatic)$, $NO_2$, CN, $CO_2H$, $CO_2(C_{1-4}aliphatic)$, $O(haloC_{1-4}\ aliphatic)$, or halo-$C_{1-4}aliphatic$, wherein each of the foregoing $C_{1-4}aliphatic$ groups of $R^o$ is unsubstituted.

An aliphatic or heteroaliphatic group, or a non-aromatic heterocyclic ring may contain one or more substituents and thus may be "optionally substituted". Unless otherwise defined above and herein, suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic group.

Unless otherwise defined above and herein, optional substituents on the nitrogen of a non-aromatic heterocyclic ring are generally selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^{+1}$)$_2$, —C(=NH)—N(R$^+$)$_2$, or —NR$^+$SO$_2$R$^+$; wherein R$^+$ is hydrogen, an optionally substituted $C_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group or the phenyl ring of R$^+$ are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —CO$_2$H, —CO$_2$(C$_{1-4}$ aliphatic), —O(halo C$_{1-4}$ aliphatic), or halo(C$_{1-4}$ aliphatic), wherein each of the foregoing C$_{1-4}$aliphatic groups of R$^+$ is unsubstituted.

The term "alkylidene chain" refers to a straight or branched carbon chain that may be fully saturated or have one or more units of unsaturation and has two points of attachment to the rest of the molecule.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W., Wuts, P. G in "Protective Groups in Organic Synthesis", Third Edition, John Wiley & Sons, New York: 1999, the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

As detailed above, in some embodiments, two independent occurrences of $R^o$ (or R$^+$, R, R' or any other variable similarly defined herein), are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

Exemplary rings that are formed when two independent occurrences of $R^o$ (or R$^+$, R, R' or any other variable similarly defined herein), are taken together with the atom(s) to which each variable is bound include, but are not limited to the following: a) two independent occurrences of $R^o$ (or R$^+$, R, R' or any other variable similarly defined herein) that are bound to the same atom and are taken together with that atom to form a ring, for example, N(R$^o$)$_2$, where both occurrences of $R^o$ are taken together with the nitrogen atom to form a piperidin-1-yl, piperazin-1-yl, or morpholin-4-yl group; and b) two independent occurrences of $R^o$ (or R$^+$, R, R' or any other variable similarly defined herein) that are bound to different atoms and are taken together with both of those atoms to form a ring, for example where a phenyl group is substituted with two occurrences of

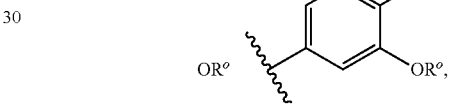

these two occurrences of $R^o$ are taken together with the oxygen atoms to which they are bound to form a fused 6-membered oxygen containing ring:

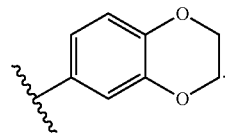 [SMILES: *c1ccc2c(c1)OCCO2]

It will be appreciated that a variety of other rings can be formed when two independent occurrences of $R^o$ (or R$^+$, R, R' or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

3. Description of Exemplary Compounds

In some embodiments of the invention, X is CH.

In other embodiments, X is N.

In one embodiment, $R^1$ is a 5-6 membered aryl or heteroaryl. Each $R^1$ ring is independently either unsubstituted or substituted with up to five J groups.

In another embodiment, $R^1$ is a 5-6 membered heteroaryl.

One embodiment of this invention is represented by formula II:

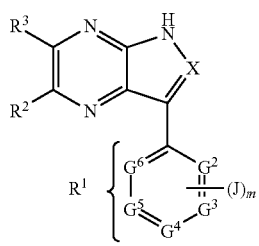

Formula II wherein $R^1$ is a 6-membered monocyclic ring wherein each G ($G^2$, $G^3$, $G^4$, $G^5$, and $G^6$) is independently CH or N; zero, one, two, or three G groups are N; and m is 0-5.

In one embodiment, one, two, or three G groups are N;

In a different embodiment $G^2$ is N.

In another embodiment any two G groups selected from $G^2$, $G^3$, $G^4$, $G^5$, and $G^6$ are N.

In yet another embodiment only one G group is N.

In another embodiment, $R^1$ is phenyl optionally substituted with up to 5 J groups.

In some embodiments of this invention, J is —U—$(R^6)_n$ wherein
each $R^6$ is independently H or optionally substituted $C_{1-12}$ aliphatic, $C_{3-10}$ cycloaliphatic, $C_{7-12}$ benzofused cycloaliphatic, $C_{6-10}$ aryl, 5-14 membered heterocyclyl, 5-14 membered heteroaryl, $OR^5$, $N(R^4)_2$, or $SR^5$;
U is a bond or an optionally substituted $C_{1-6}$ aliphatic wherein up to two methylene units are optionally replaced by Y in a chemically stable arrangement;
Y is a group selected from —O—, —$NR^5$—, —S—, —$NR^5$C(O)—, —N(SO$_2$)—, —$NR^5$C(O)NR$^5$—, —C(O)NR$^5$—, —C(O)—, —OC(O)NR$^5$—, —NR$^5$C(O)O—, —C(O)O—, or —OC(O)—; and
n is 1 or 2.

In one embodiment of this invention, Y is —O—, or —S—.

In another embodiment, Y—NR$^5$(C=O)— or —(C=O)NR$^5$—;

In another embodiment Y is —NR$^5$—.

In yet another embodiment one methylene unit of U is replaced by Y.

In another embodiment U is —Y—(C$_{1-5}$aliphatic)-. In some embodiments, Y is bonded to $R^1$ and C$_{1-5}$aliphatic is bonded to $R^6$. In other embodiments, Y is bonded to $R^6$ and C$_{1-5}$aliphatic is bonded to $R^1$.

Some embodiments are represented by the compound in formula III wherein $G^3$ is carbon and J is substituted in the 3-position as shown:

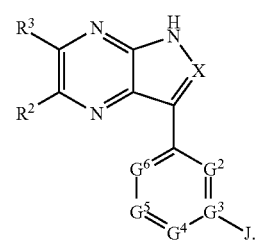

Formula III

In some embodiments J is —U—$(R^6)_n$.

In one embodiment of this invention, $R^6$ is optionally substituted $C_{3-10}$ cycloaliphatic or $C_{7-12}$ benzofused cycloaliphatic.

In another embodiment $R^6$ is an optionally substituted 5-6 membered aryl or heteroaryl. In some embodiments, $R^6$ is an optionally substituted 5-6 membered aryl; in other embodiments $R^6$ is an optionally substituted 5-6 membered heteroaryl.

In another embodiment, $R^6$ is optionally substituted phenyl.

In yet another embodiment $R^6$ is an optionally substituted 5-6 membered heterocyclyl.

In some embodiments U is a bond.

In other embodiments U is $C_{1-3}$ aliphatic wherein zero methylene units are replaced.

In one embodiment U is —NRCH(CH$_3$)— wherein the methyl group is in the S conformation. It would be understood that the atom of —NRCH(CH$_3$)— that is bound to formula I, formula II, or formula III is the "—N" atom.

In another embodiment $R^6$ is substituted with halogen, $C_{1-6}$aliphatic, $C_{1-6}$alkoxy, —CN, —N(R$^5$)$_2$, —C(O)R$^5$, —NC(O)R$^5$, —C(O)NR$^5$, —C(O)OR$^5$, —SOR$^5$, or —SO$_2$R$^5$.

In another embodiment of this invention, $R^2$ and $R^3$ are each independently V—R.

In one embodiment $R^2$ and $R^3$ are each independently V—R$^a$.

In another embodiment $R^2$ and $R^3$ are each independently V—R$^b$.

In another embodiment V is a $C_{1-2}$ aliphatic chain; one methylene unit of V is replaced by Q; and Q is selected from —O—, —NR$^5$—, —S—, —C(O)O—, and —NR$^5$C(O)—.

In another embodiment, V is an optionally substituted $C_{1-6}$ aliphatic chain wherein one methylene unit is replaced by Q in a chemically stable arrangement wherein Q is —CONR$^5$— or —O(CH$_2$)—.

In yet another embodiment, V is Q wherein Q is —C(O)— or —SO$_2$—.

In some embodiments $R^2$ and $R^3$ are each independently hydrogen, halogen, CN, or V—R wherein V is —C(O)O—, —NH—, —N(CH$_3$)—, —N(CH$_2$CH$_3$)—, —N(CH (CH$_3$)$_2$)—, —O(CH$_2$)$_2$O—, —C(O)NH—, —C(O)O—, —O—, —CH$_2$O—, —NHC(O)—, —SO$_2$NH—, or —SO$_2$N (CH$_3$)—.

In other embodiments V—R is —C(O)OH, —C(O)OR$^5$, —O(CH$_2$)$_2$OCH$_3$, —C(O)OCH$_3$, —OH, —CH$_2$OH, —NHC (O)CH$_3$, —SO$_2$NH$_2$, or —SO$_2$N(Me)$_2$.

In other embodiments V—R is —C(O)OH, —C(O)O (C$_{1-6}$alkyl), —O(CH$_2$)$_2$O(C$_{1-6}$alkyl), —C(O)O(C$_{1-6}$alkyl), —OH, —CH$_2$OH, —C(O)NH$_2$, —C(O)NH(C$_{1-6}$alkyl), —C(O)N(C$_{1-6}$alkyl)$_2$, —SO$_2$NH$_2$, —SO$_2$NH(C$_{1-6}$alkyl), or —SO$_2$N(C$_{1-6}$alkyl)$_2$.

In certain embodiments V is a bond.

In some embodiments, R is H. In other embodiments R is H or methyl.

In certain embodiments R$^b$ is N(R$^4$)$_2$.

In certain other embodiments, R$^a$ is 5-6 membered aryl or heteroaryl.

In yet other embodiments R$^2$ and R$^3$ are each independently H, halogen, CN,

V—R$^b$ wherein V is a bond and R$^b$ is —N(R$^4$)$_2$, or

V—R$^a$ wherein V is a bond and R$^a$ is 5-6 membered aryl or 5-6 membered heteroaryl.

In some embodiments R$^2$ and R$^3$ are each independently halogen.

In other embodiments, R$^2$ and R$^3$ are each independently chlorine.

In some embodiments R$^2$ and R$^3$ are each independently substituted with up to three occurrences of R$^7$.

In other embodiments at least one of R$^2$ and R$^3$ is H.

In certain embodiments R$^3$ is H.

In some embodiments, n is 0-3; in other embodiments 0-2; and in yet other embodiments, 0-1.

Representative examples of compounds of this invention are set forth below in Table I.

TABLE I

Examples of Compounds of Formulae I, II, and III

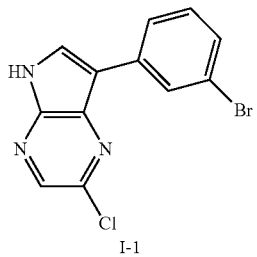

I-1

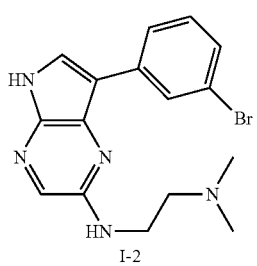

I-2

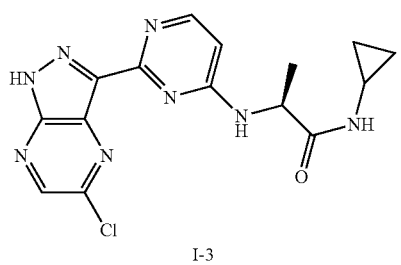

I-3

TABLE I-continued

Examples of Compounds of Formulae I, II, and III

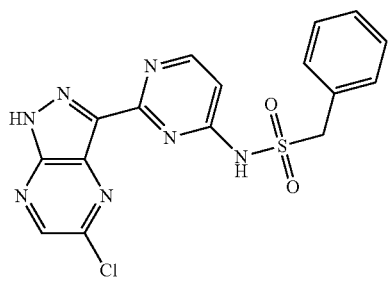 [SMILES: O=S(=O)(Cc1ccccc1)Nc1ccnc(-c2n[nH]c3ncc(Cl)nc23)n1]

I-4

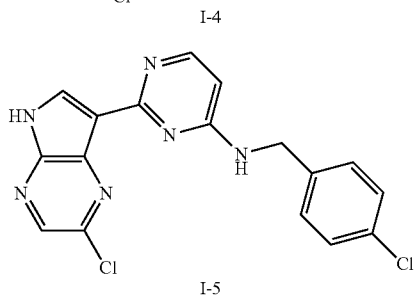

I-5

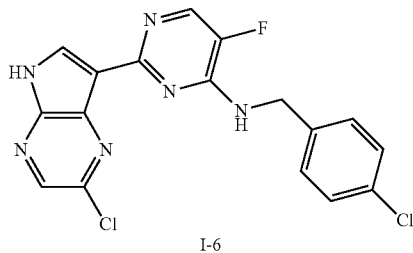

I-6

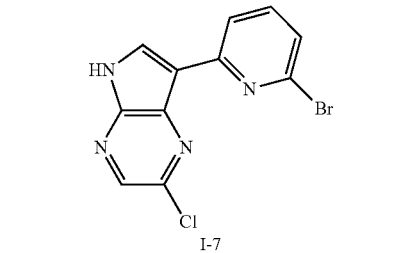

I-7

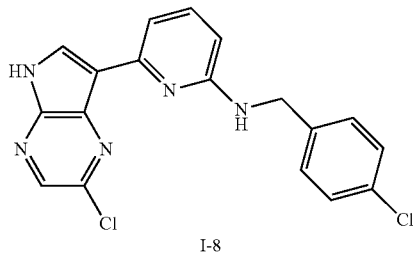

I-8

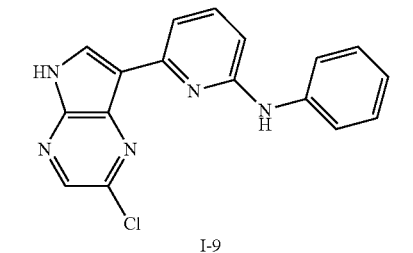

I-9

TABLE I-continued
Examples of Compounds of Formulae I, II, and III
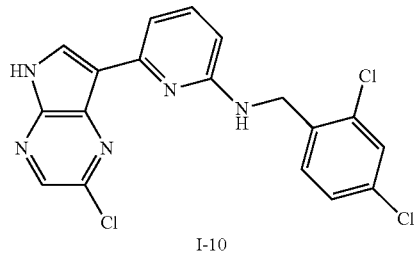
I-10
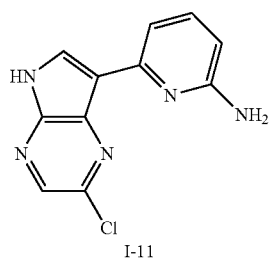
I-11
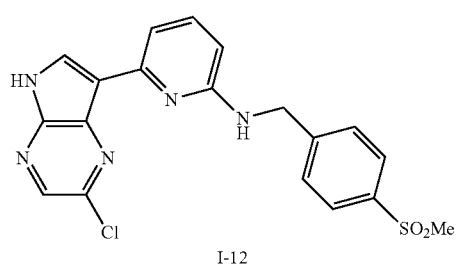
I-12
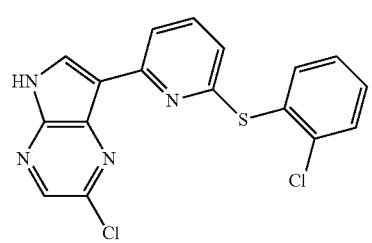 [SMILES: Clc1cnc2[nH]cc(-c3cccc(Sc4ccccc4Cl)n3)c2n1]
I-13
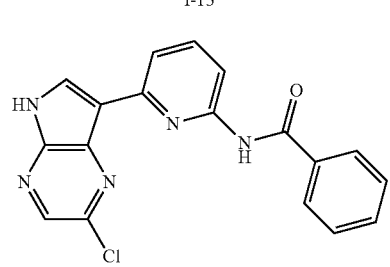
I-14
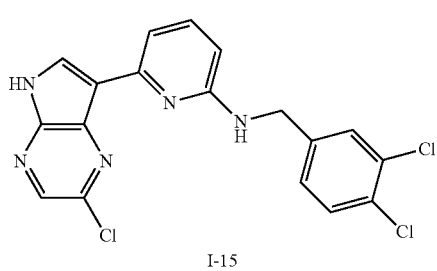
I-15
TABLE I-continued
Examples of Compounds of Formulae I, II, and III
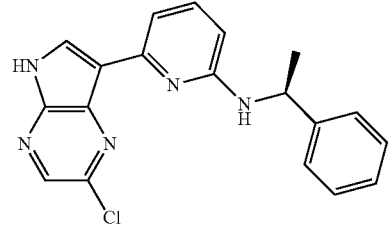 [SMILES: C[C@H](Nc1cccc(-c2c[nH]c3ncc(Cl)nc23)n1)c1ccccc1]
I-16
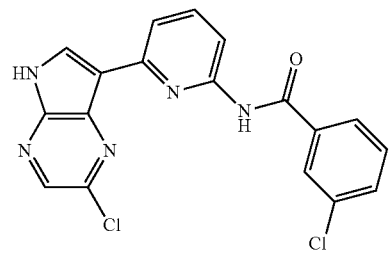 [SMILES: O=C(Nc1cccc(-c2c[nH]c3ncc(Cl)nc23)n1)c1cccc(Cl)c1]
I-17
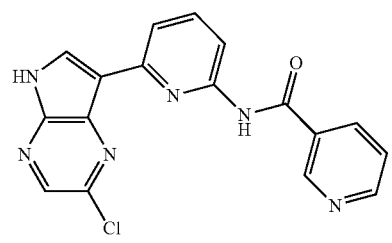 [SMILES: O=C(Nc1cccc(-c2c[nH]c3ncc(Cl)nc23)n1)c1cccnc1]
I-18
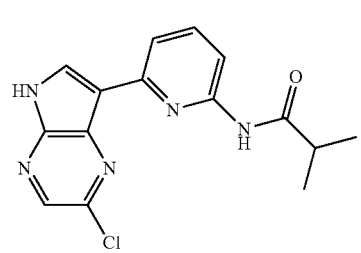 [SMILES: CC(C)C(=O)Nc1cccc(-c2c[nH]c3ncc(Cl)nc23)n1]
I-19
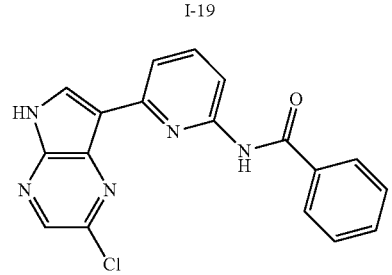
I-20
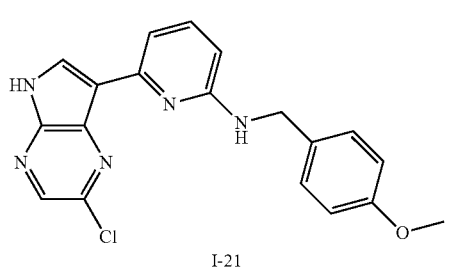
I-21

TABLE I-continued
Examples of Compounds of Formulae I, II, and III
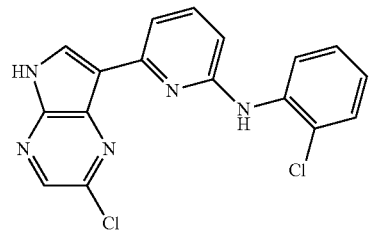 [SMILES: Clc1cnc2[nH]cc(-c3cccc(Nc4ccccc4Cl)n3)c2n1]
I-22
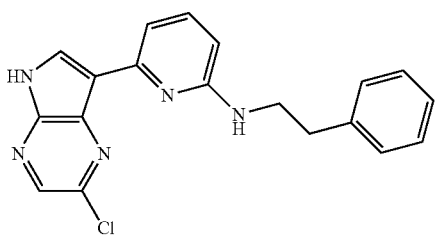 [SMILES: Clc1cnc2[nH]cc(-c3cccc(NCCc4ccccc4)n3)c2n1]
I-23
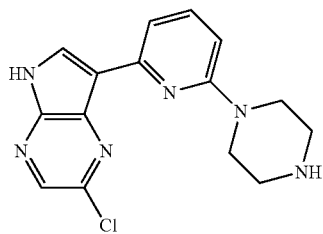 [SMILES: Clc1cnc2[nH]cc(-c3cccc(N4CCNCC4)n3)c2n1]
I-24
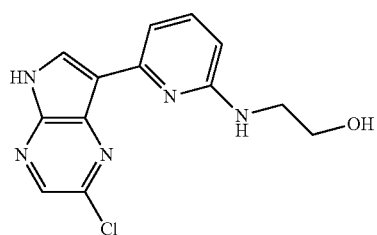 [SMILES: OCCNc1cccc(-c2c[nH]c3ncc(Cl)nc23)n1]
I-25
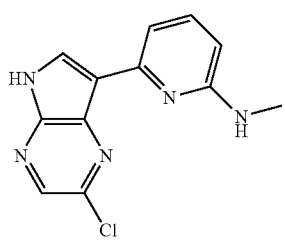 [SMILES: CNc1cccc(-c2c[nH]c3ncc(Cl)nc23)n1]
I-26
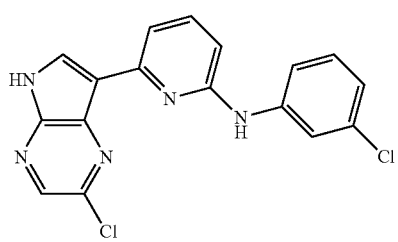 [SMILES: Clc1cccc(Nc2cccc(-c3c[nH]c4ncc(Cl)nc34)n2)c1]
I-27
TABLE I-continued
Examples of Compounds of Formulae I, II, and III
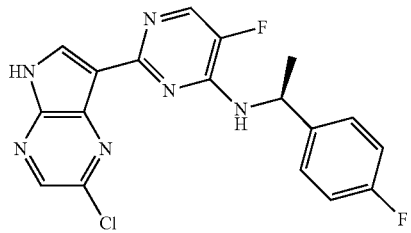
I-28
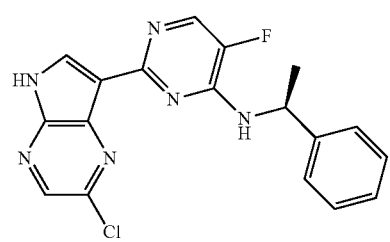 [SMILES: C[C@H](Nc1nc(-c2c[nH]c3ncc(Cl)nc23)ncc1F)c1ccccc1]
I-29
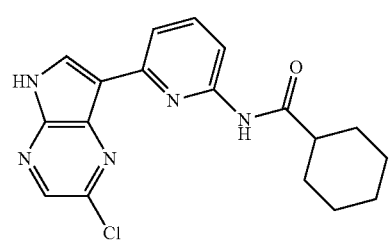 [SMILES: O=C(Nc1cccc(-c2c[nH]c3ncc(Cl)nc23)n1)C1CCCCC1]
I-30
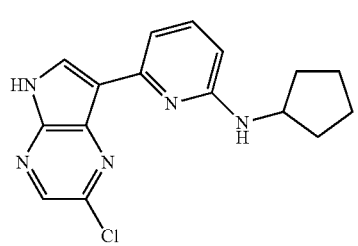 [SMILES: Clc1cnc2[nH]cc(-c3cccc(NC4CCCC4)n3)c2n1]
I-31
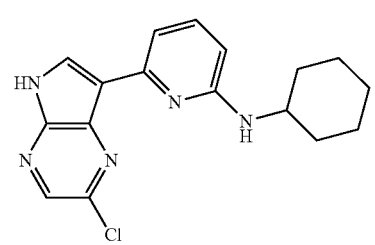 [SMILES: Clc1cnc2[nH]cc(-c3cccc(NC4CCCCC4)n3)c2n1]
I-32
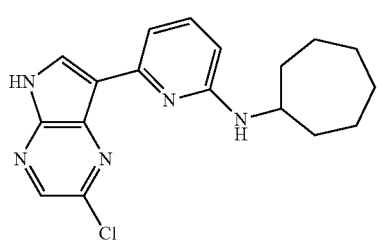 [SMILES: Clc1cnc2[nH]cc(-c3cccc(NC4CCCCCC4)n3)c2n1]
I-33

TABLE I-continued

Examples of Compounds of Formulae I, II, and III

I-34

I-35

I-36

I-37

I-38

I-39

I-40

I-41

I-42

TABLE I-continued
Examples of Compounds of Formulae I, II, and III
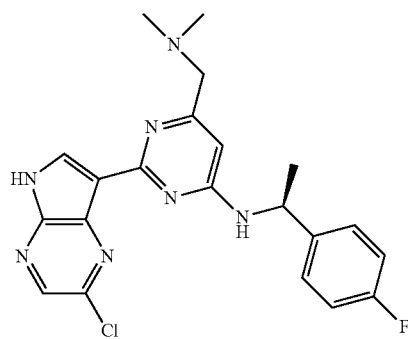 [SMILES: C[C@H](Nc1cc(CN(C)C)nc(-c2c[nH]c3ncc(Cl)nc23)n1)c1ccc(F)cc1]
I-43
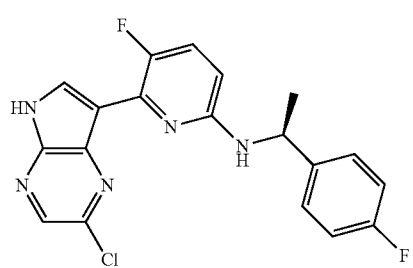 [SMILES: C[C@H](Nc1ccc(F)c(-c2c[nH]c3ncc(Cl)nc23)n1)c1ccc(F)cc1]
I-44
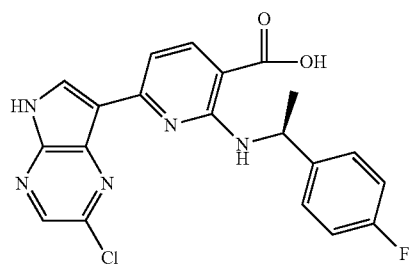 [SMILES: C[C@H](Nc1nc(-c2c[nH]c3ncc(Cl)nc23)ccc1C(=O)O)c1ccc(F)cc1]
I-45
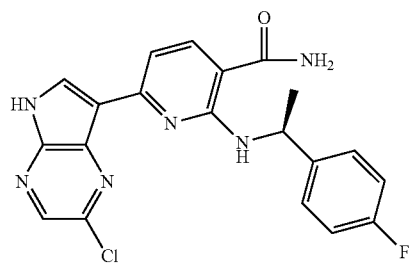 [SMILES: C[C@H](Nc1nc(-c2c[nH]c3ncc(Cl)nc23)ccc1C(N)=O)c1ccc(F)cc1]
I-46
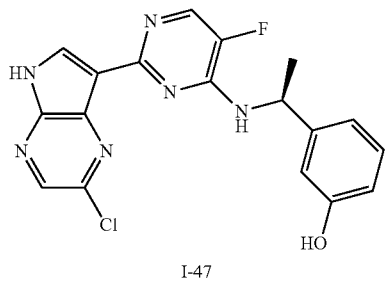
I-47
TABLE I-continued
Examples of Compounds of Formulae I, II, and III
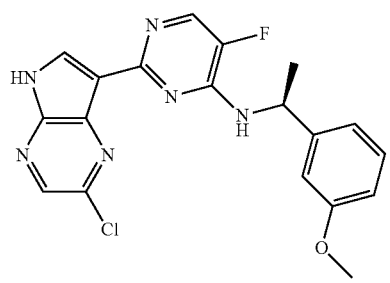 [SMILES: COc1cccc([C@H](C)Nc2nc(-c3c[nH]c4ncc(Cl)nc34)ncc2F)c1]
I-48
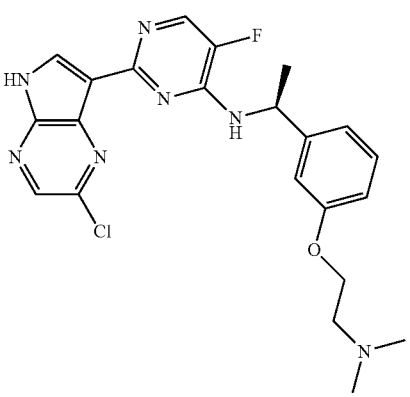 [SMILES: C[C@H](Nc1nc(-c2c[nH]c3ncc(Cl)nc23)ncc1F)c1cccc(OCCN(C)C)c1]
I-49
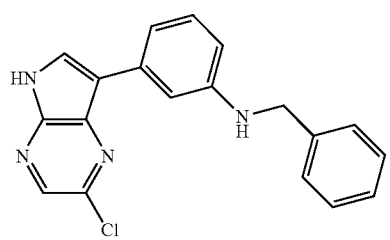 [SMILES: Clc1cnc2[nH]cc(-c3cccc(NCc4ccccc4)c3)c2n1]
I-50
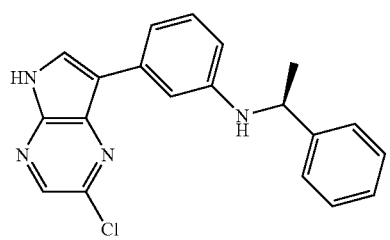 [SMILES: C[C@H](Nc1cccc(-c2c[nH]c3ncc(Cl)nc23)c1)c1ccccc1]
I-51
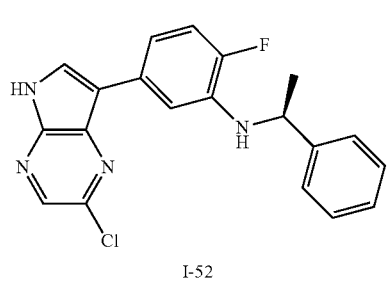
I-52

TABLE I-continued
Examples of Compounds of Formulae I, II, and III
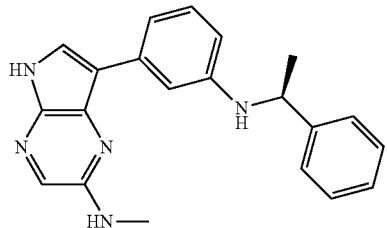 [SMILES: CNc1cnc2[nH]cc(-c3cccc(N[C@@H](C)c4ccccc4)c3)c2n1]
I-53
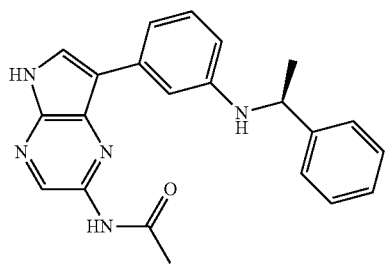 [SMILES: CC(=O)Nc1cnc2[nH]cc(-c3cccc(N[C@@H](C)c4ccccc4)c3)c2n1]
I-54
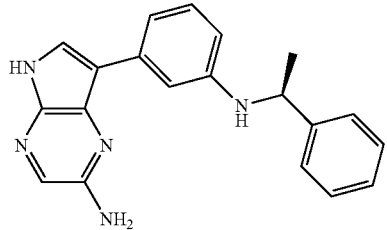 [SMILES: C[C@H](Nc1cccc(-c2c[nH]c3ncc(N)nc23)c1)c1ccccc1]
I-55
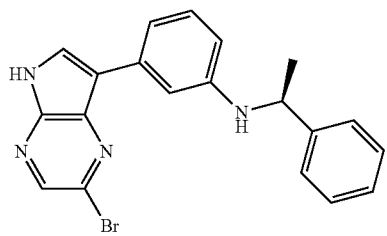 [SMILES: C[C@H](Nc1cccc(-c2c[nH]c3ncc(Br)nc23)c1)c1ccccc1]
I-56
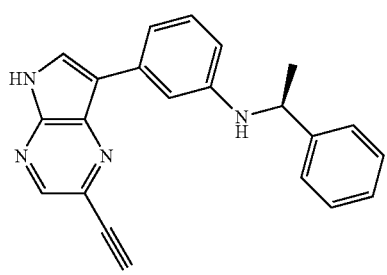 [SMILES: C#Cc1cnc2[nH]cc(-c3cccc(N[C@@H](C)c4ccccc4)c3)c2n1]
I-57
TABLE I-continued
Examples of Compounds of Formulae I, II, and III
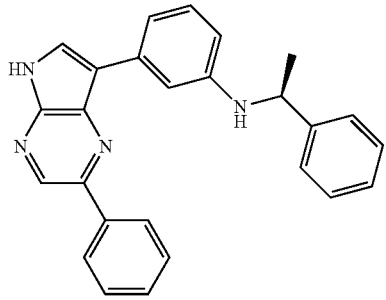 [SMILES: C[C@H](Nc1cccc(-c2c[nH]c3ncc(-c4ccccc4)nc23)c1)c1ccccc1]
I-58
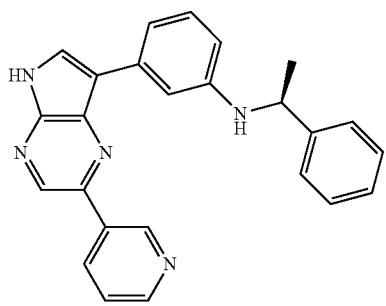 [SMILES: C[C@H](Nc1cccc(-c2c[nH]c3ncc(-c4cccnc4)nc23)c1)c1ccccc1]
I-59
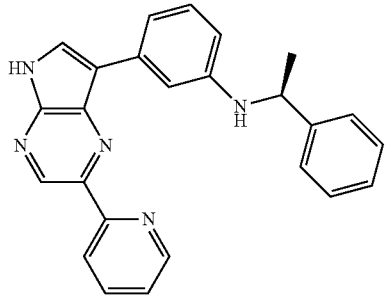 [SMILES: C[C@H](Nc1cccc(-c2c[nH]c3ncc(-c4ccccn4)nc23)c1)c1ccccc1]
I-60
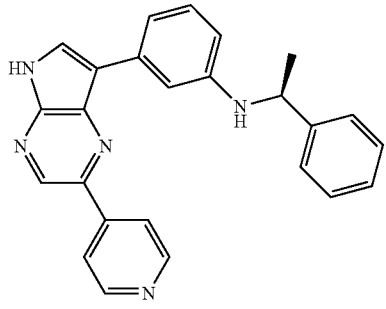 [SMILES: C[C@H](Nc1cccc(-c2c[nH]c3ncc(-c4ccncc4)nc23)c1)c1ccccc1]
I-61
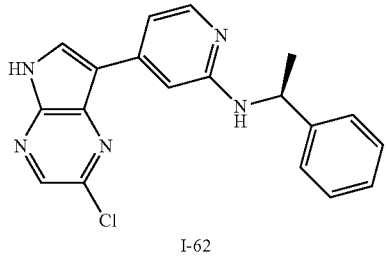
I-62

TABLE I-continued
Examples of Compounds of Formulae I, II, and III
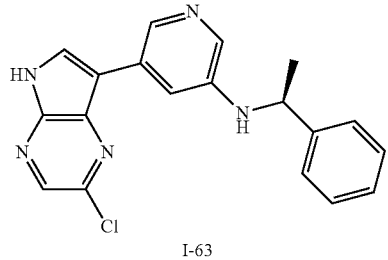
I-63
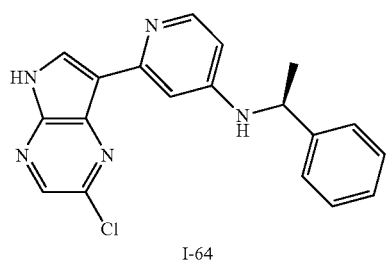
I-64
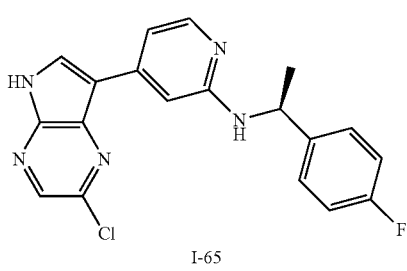
I-65
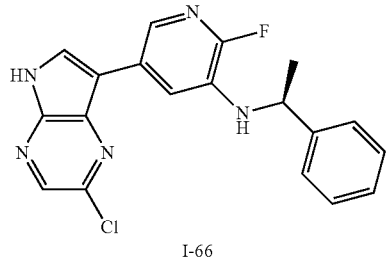
I-66
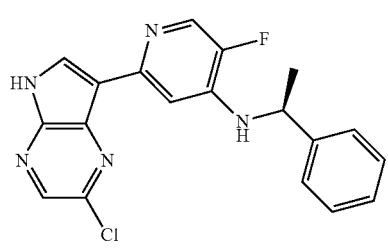 [SMILES: C[C@H](Nc1cc(-c2c[nH]c3ncc(Cl)nc23)ncc1F)c1ccccc1]
I-67
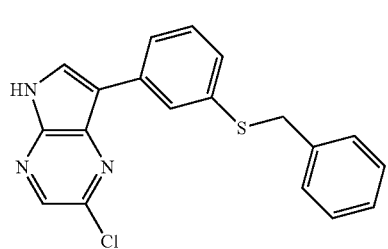 [SMILES: Clc1cnc2[nH]cc(-c3cccc(SCc4ccccc4)c3)c2n1]
I-68
TABLE I-continued
Examples of Compounds of Formulae I, II, and III
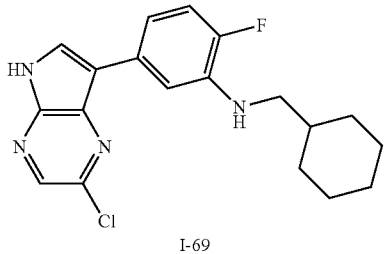
I-69
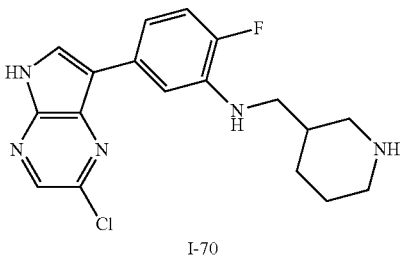
I-70
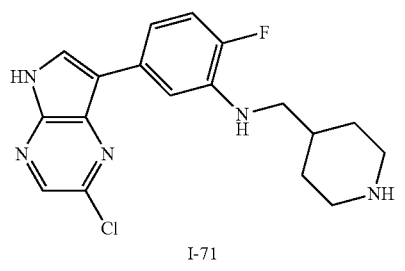
I-71
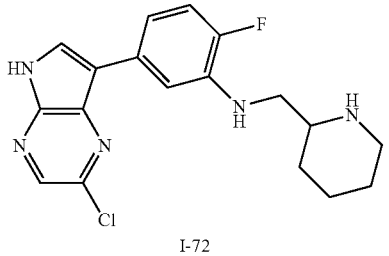
I-72
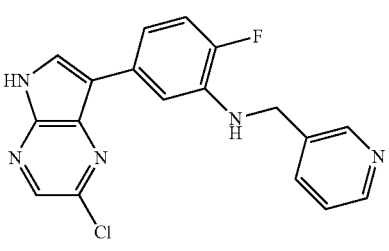 [SMILES: Fc1ccc(-c2c[nH]c3ncc(Cl)nc23)cc1NCc1cccnc1]
I-73
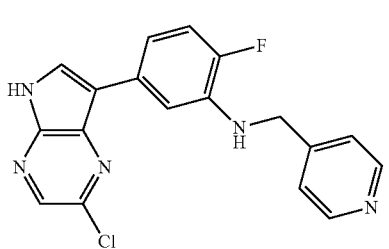 [SMILES: Fc1ccc(-c2c[nH]c3ncc(Cl)nc23)cc1NCc1ccncc1]
I-74

TABLE I-continued
Examples of Compounds of Formulae I, II, and III
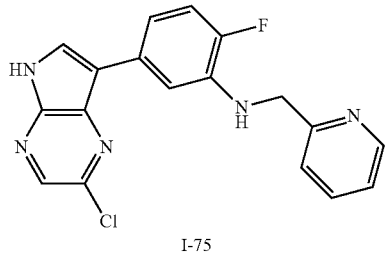
I-75
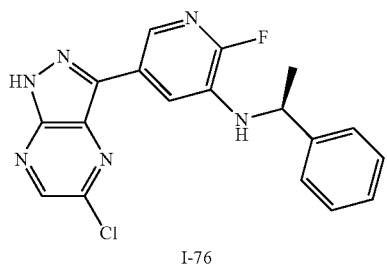
I-76
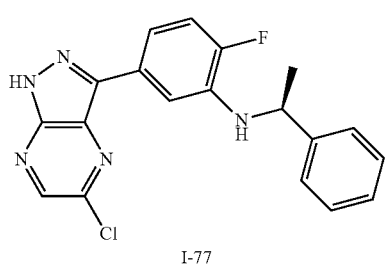
I-77
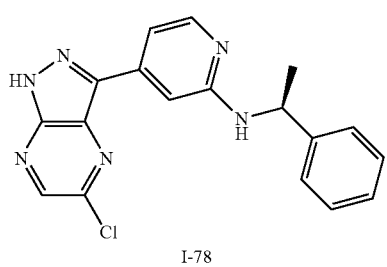
I-78
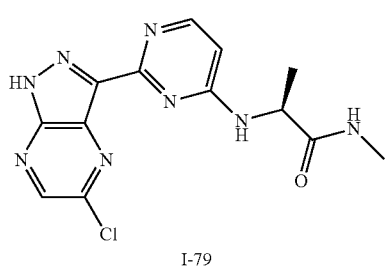
I-79
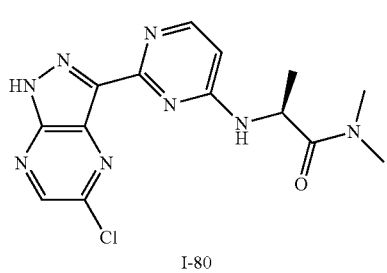
I-80
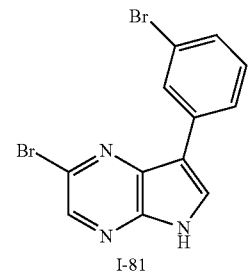
I-81
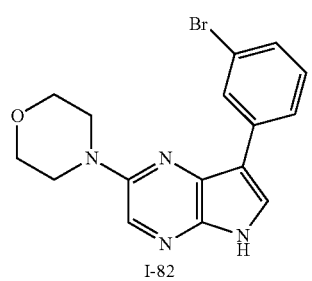
I-82
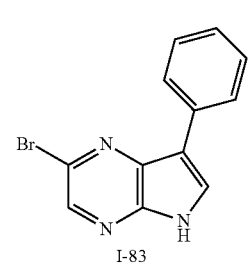
I-83
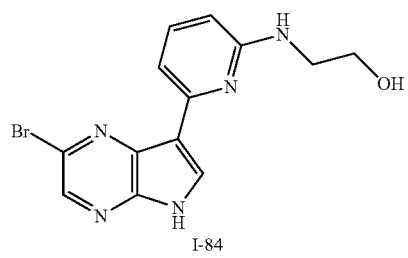
I-84
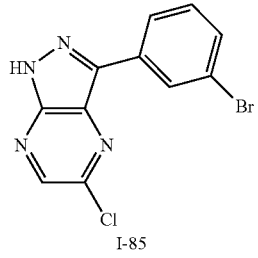
I-85
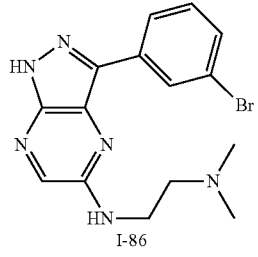
I-86

4. General Synthetic Methodology:

The compounds of this invention may be prepared in general by methods known to those skilled in the art for analogous compounds and as illustrated by Scheme I below. These compounds may be analyzed by known methods, including but not limited to LCMS (liquid chromatography mass spectrometry), HPLC (high performance liquid chromatography) and NMR (nuclear magnetic resonance).

It should be understood that the specific conditions shown below are only examples, and are not meant to limit the scope of the conditions that can be used for making compounds of this invention. Instead, this invention also includes conditions known to those skilled in that art for making the compounds of this invention. Starting materials shown are either commercially available or can be readily accessible from methods known to one skilled in the art. Unless otherwise indicated, all variables in the following schemes are as defined herein.

Scheme I

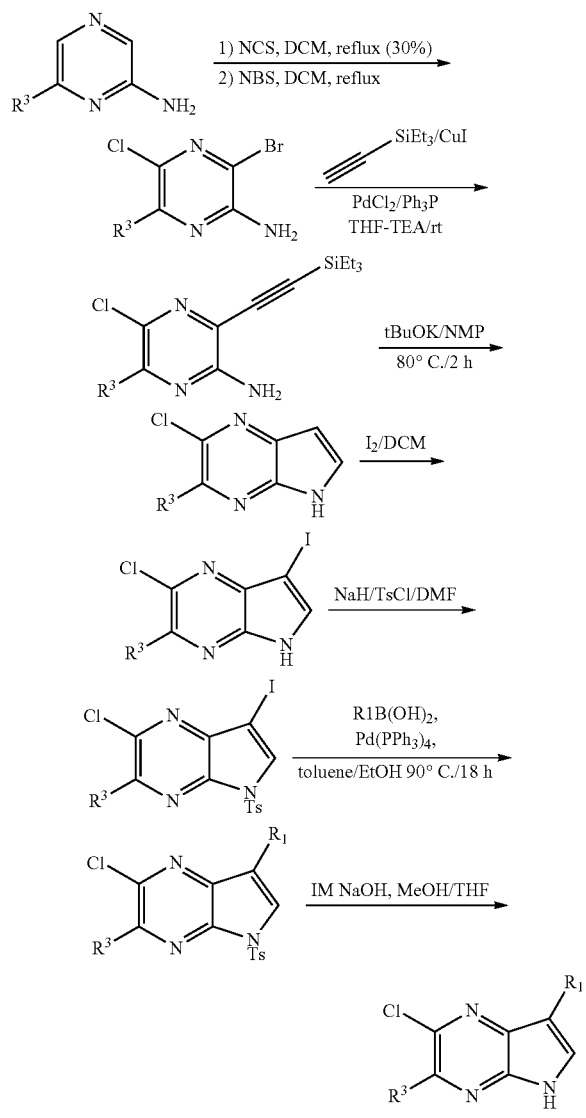

EXAMPLE I-1

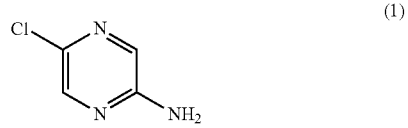

5-Chloro-pyrazin-2-ylamine (1): A 250 ml round bottom flask was charged with 2-aminopyrazine (10 g, 0.1 mol), N-chlorosuccinimide (14 g, 0.1 mol) and dichloromethane (100 ml) under nitrogen. The reaction mixture was refluxed for 5 h, then allowed to cool to room temperature. The reaction mixture was filtered though a 1 cm thick celite pad, which was then thoroughly washed with dichloromethane. The organic was concentrated in vacuo and the compound was purified by flash chromatography, using as eluent pentane/EtOAc 0% to 50%, to give the title compound (3 g, 22%). 1H NMR (CDCl$_3$) 4.5-4.8 (2H, brs), 7.8 (1H, s), 8.0 (1H, s).

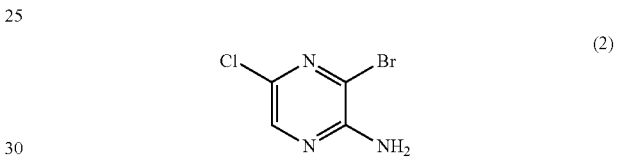

3-Bromo-5-chloro-pyrazin-2-ylamine (2): A 250 ml round bottom flask was charged with 5-chloro-pyrazin-2-ylamine (1) (3 g, 23 mmol, N-bromosuccinimide (4 g, 23 mmol) and dichloromethane (100 ml) under nitrogen. The reaction mixture was refluxed for 1 h, then allowed to cool to room temperature and concentrated in vacuo. The compound was purified by flash chromatography, using as eluent pentane/EtOAc 0% to 50%, to give the title compound (3 g, 62%). 1H NMR (DMSo-d6) 6.8-6.9 (2H, brs), 8.0 (1H, s). MS (ES+): 210, 212.

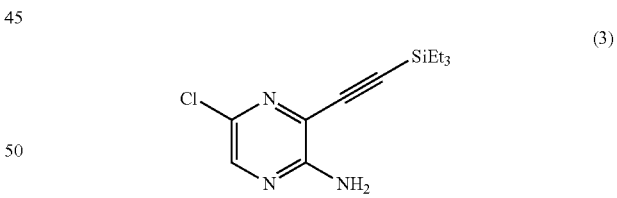

5-Chloro-3-(triethyl-silanylethynyl)-pyrazin-2-ylamine (3): A 250 ml round bottom flask was charged with 3-bromo-5-chloro-pyrazin-2-ylamine (2) (1 g, 4.8 mmol), THF (10 ml), copper iodide (9 mg, 0.05 mM) and PdCl$_2$(PPh$_3$)$_2$ (34 mg, 0.05 mmol) under nitrogen. To the reaction mixture, triethylamine (2 ml, 14.4 mmol) and triethylsilylacetylene (1 ml, 5.76 mmol) were added. The reaction mixture was stirred at room temperature for 3 h, then concentrated in vacuo and the residue was purified by flash chromatography, using as eluent pentane/EtOAc 10% to 30%, to give the title compound as an off white solid (1.2 g, 100%). 1H NMR (CDCl$_3$): 0.7-0.8 (6H, qd), 1.0-1.1 (9H, t), 5.0-5.1 (2H, brs), 7.95 (1H, s). MS (ES+): 268.

(4)

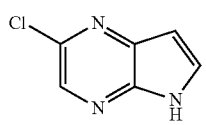

2-Chloro-5H-pyrrolo[2,3-b]pyrazine (4): A solution of potassium tert-butoxide (1 g, 4.5 mM) in N-methylpyrrolidone (3 ml) was heated to 80° C. under nitrogen. A solution of 5-chloro-3-(triethyl-silanylethynyl)-pyrazin-2-ylamine (3) (1.2 g, 4.5 mmol) in N-methylpyrrolidone (10 ml) was added dropwise. The reaction mixture was stirred at 80° C. for a further fifty minutes and then the reaction mixture was allowed to cool to room temperature. Brine (10 ml) was added to the reaction mixture and extracted with ethyl acetate (5×20 ml). The combined organics were washed with brine, dried over magnesium sulfate and concentrated in vacuo to afford the title compound as a solution in N-methylpyrrolidone. MS (ES+): 154

(5)

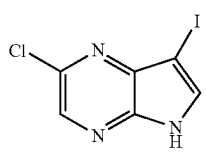

2-Chloro-7-iodo-5H-pyrrolo[2,3-b]pyrazine (5): A 1M solution of iodine chloride in dichloromethane (4 ml, 4 mmol) was added dropwise to an ice-cold solution of 2-chloro-5H-pyrrolo[2,3-b]pyrazine (4) in N-methylpyrrolidone (residual from previous step) and pyridine (5 ml). The reaction mixture was stirred for 60 minutes at 0° C. and then was concentrated in vacuo. The residue was purified by flash chromatography, using as eluent pentane/EtOAc 0% to 50%, to give the title compound (820 mg, 75% over two steps). 1H NMR (DMSO-d6) 8.2 (1H, s), 8.4 (1H, s). MS (ES+): 280

(6)

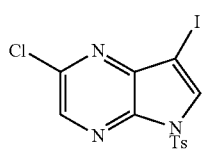

2-Chloro-7-iodo-5-(toluene-4-sulfonyl)-5H-pyrrolo[2,3-b]pyrazine (6): Sodium hydride (140 mg, 3.5 mmol) was added to an ice-cold solution of 2-chloro-7-iodo-5H-pyrrolo[2,3-b]pyrazine (5) (820 mg, 2.9 mmol) in dimethylformamide (7 ml) under nitrogen. After 30 minutes tosyl chloride (570 mg, 3 mmol) was added to the reaction mixture and the reaction mixture was stirred at room temperature for 18 h. The reaction mixture was then quenched with water (~15 ml). An off white solid was filtered off and dried in vacuo (950 mg, 75%). MS (ES+) 434.

(7)

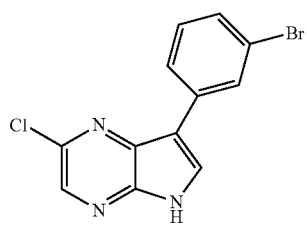

7-(3-Bromo-phenyl)-2-chloro-5H-pyrrolo[2,3-b]pyrazine (7): A 50 ml round bottom flask was charged under nitrogen with 2-chloro-7-iodo-5-(toluene-4-sulfonyl)-5H-pyrrolo[2, 3-b]pyrazine (6) (950 mg, 2.2 mmol), 3-bromophenyl boronic acid (440 mg, 2.2 mmol), tetrakis-triphenylphosphine palladium (50 mg, 0.04 mmol), 2M aqueous potassium carbonate (2.2 ml, 4.4 mmol) in a toluene/ethanol mixture (15/3 ml) under nitrogen. The reaction mixture was refluxed for 18 h, then allowed to cool to room temperature. The solution was diluted with ethyl acetate (~70 ml). The organic was washed with brine, dried over magnesium sulfate and concentrated in vacuo, The residue was triturated in dichloromethane/methanol. A pale yellow solid was removed by filtration (300 mg). The residue was taken up in a tetrahydrofuran/methanol/1M NaOH mixture (4/1/1 ml) and stirred at room temperature for 2 h. The reaction mixture was diluted with ethyl acetate, washed with brine, dried over magnesium sulfate and concentrated in vacuo. The residue was triturated in methanol. A solid was filtered off as the title compound (10 mg, 1%). 1H NMR (DMSO-d6): 7.35-7.45 (2H, m), 8.10-8.15 (1H, d), 8.35 (1H, s), 8.4 (1H, s), 8.6 (1H, s). MS (ES+): 310, 312.

Scheme II

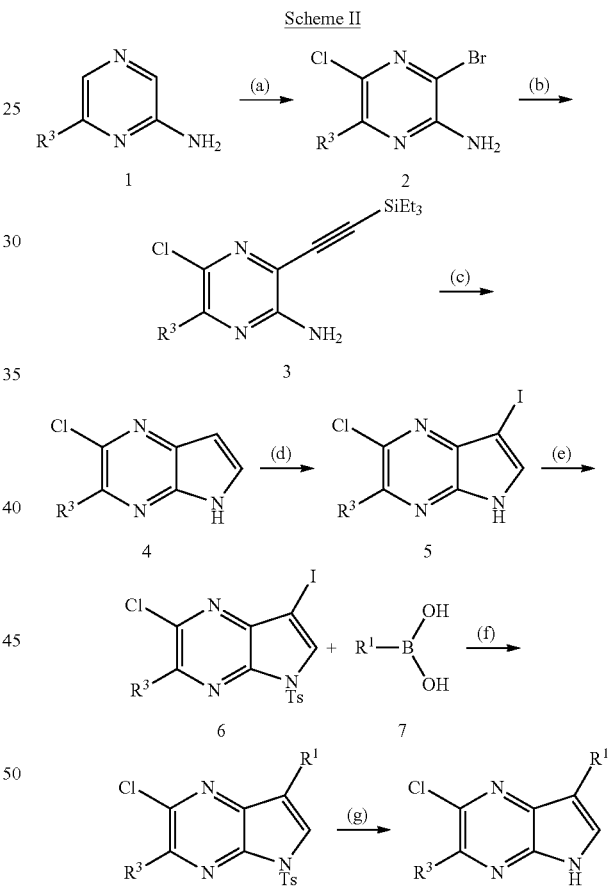

Reagents and conditions:
(a) i) NCS, DCM, reflux
 ii) NBS, DCM, reflux;
(b) triethylsilylacetylene, copper(I) iodide, PdCl$_2$(PPh$_3$)$_2$, Et$_3$N, THF;
(c) $^t$BuOK, NMP, 80° C., 2 h;
(d) I$_2$ DCM;
(e) NaH, TsCl, DMF;
(f) Pd(PPh$_3$)$_4$, toluene, EtOH, 90° C., 18 hours;
(g) 1 M NaOH, MeOH, THF.

Scheme II above shows a general synthetic route that is used for preparing the compounds 9 of this invention when R$^1$ and $R^3$ are as described herein. Intermediates 2, prepared by successive chlorination and bromination of derivatives 1, are treated with triethylsilylacetylene under Sonogashira conditions that are well known to the one in the art. Cyclisation of intermediates 3 furnishes compounds of structure 4. Intermediates 6 are prepared by iodination of compounds of structure 4 followed by subsequent protection of intermediates 5 with a tosyl group. The formation of derivatives 8 is achieved by treating the iodide 6 with boronic acid derivatives 7 in the presence of palladium as a catalyst by using the Suzuki coupling methods that are well known in the art. The reaction is amenable to a variety of boronic acid 7. Finally, the tosyl protective group is removed under basic conditions, according to Scheme II step (g), to afford compounds of structure 9.

Scheme III

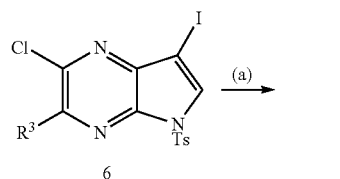

6

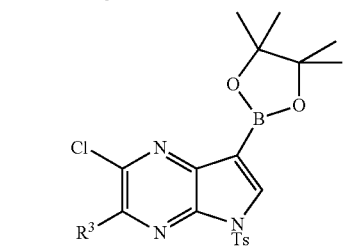

10    11

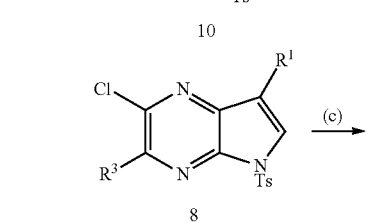

8    9

Reagents and conditions:
(a) PdCl$_2$(dppf)$_2$, dioxane, KOAc, bis(pinacolato)diboron, 18 hours;
(b) Pd(PPh$_3$)$_4$, Na$_2$CO$_3$, DME, EtOH/H$_2$O, microwave irradiation, 120° C., 2 hours;
(c) 1 M NaOH, MeOH, THF.

Scheme III above shows a general synthetic route that is used for preparing the compounds 9 of this invention when $R^1$ and $R^3$ are as described herein. Boronic esters 10 are formed according to Scheme III step (a). The formation of derivatives 8 is achieved by treating the bromide 11 with boronic ester derivatives 10 in the presence of palladium as a catalyst by using the Suzuki coupling methods that are well known in the art. The reaction is amenable to a variety of substituted aryl or heteroaryl bromides 11. Finally, the tosyl protective group is removed under basic conditions, according to Scheme II step (c), to afford compounds of structure 9.

Scheme IV

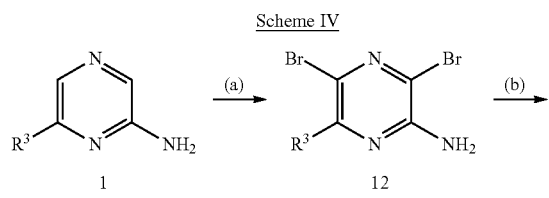

1    12

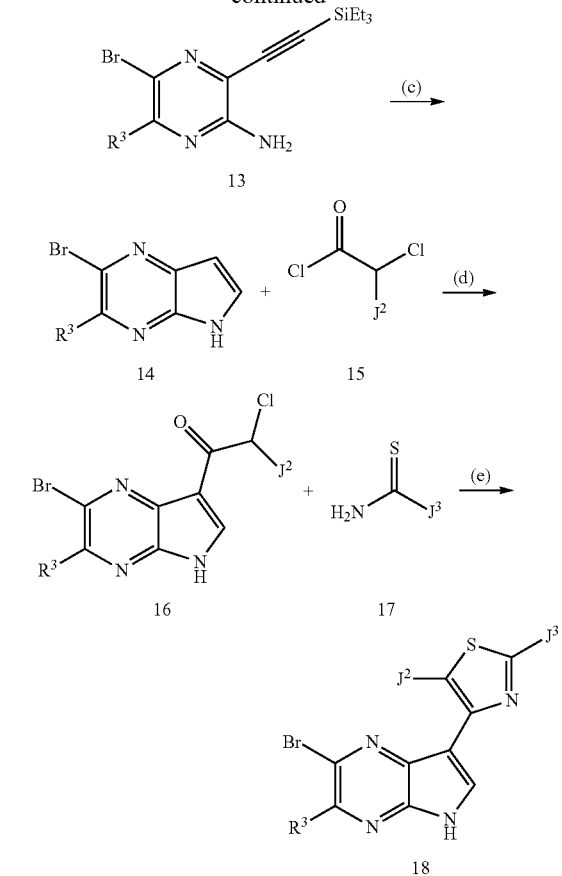

Reagents and conditions:
(a) NBS, DCM, 0° C. then reflux, 4 hours;
(b) triethylsilylacetylene, copper(I) iodide, PdCl$_2$(PPh$_3$)$_2$, Et$_3$N, THF;
(c) $^t$BuOK, NMP, 80° C., 2 h;
(d) AlCl$_3$, CH$_2$Cl$_2$, RT, 16 hours;
(e) EtOH, microwave irradiations, 120° C., 10 mins.

Scheme IV above shows a general synthetic route that is used for preparing the compounds 18 of this invention when $R^3$ is as described herein. $J^2$ and $J^3$ correspond to J as defined herein. Intermediates 12, obtained by dibromination of derivatives 1, are treated with triethylsilylacetylene under Sonogashira conditions that are well known to the one in the art. Cyclisation of intermediates 13 furnishes compounds of structure 14. Intermediates 16 are prepared by using the Friedel-Craft acylation methods that are well known in the art. This reaction is amenable to a variety of substituted chloroacetyl chlorides 15 to form compounds of formula 16. Finally, compounds of formula 18 are obtained by cyclisation of intermediate 16 according to Scheme IV step (e).

Scheme V

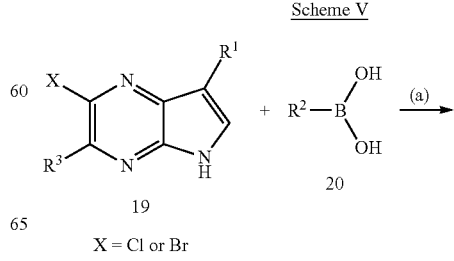

19    20

X = Cl or Br

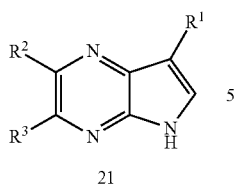

Reagents and conditions: (a) Pd(PPh₃)₄, toluene, EtOH, 90° C., 18 hours.

Scheme V above shows a general synthetic route that is used for preparing the compounds 21 of this invention when $R^1$, $R^2$ and $R^3$ are as described herein. Compounds of structure 19 are treated with a boronic acid derivative 20 in the presence of palladium as a catalyst by using the Suzuki coupling method which is well known in the art. The reaction is amenable to a variety of boronic acids 20.

Scheme VI

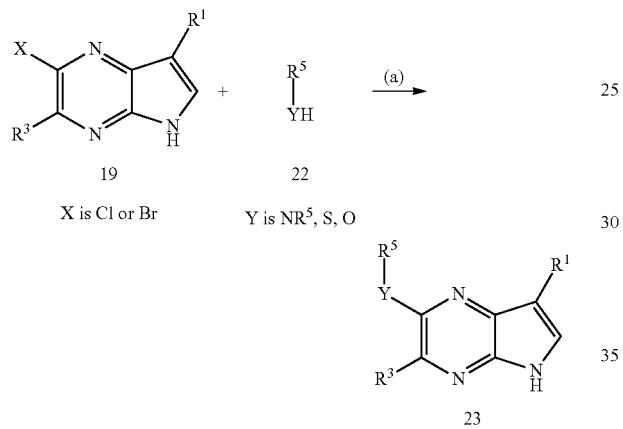

Reagents and conditions:
(a) PdCl₂(dppf), NaOᵗBu, THF, heating; or Cu, K₂CO₃, nitrobenzene, heating; or microwave irradiations, 180° C., 4 hours.

Scheme VI above shows a general synthetic route that is used for preparing the compounds 23 of this invention when $R^1$, $R^3$, and $R^5$ are as described herein. —Y—$R^5$ as described in Scheme V corresponds to $R^2$ as defined herein. Compounds of formula 19 are treated with a nucleophile 22 in the presence of palladium as a catalyst by using the Buchwald-Hartwig cross coupling reaction well known in the art. This cross coupling reaction could also be achieved by treating compounds 19 with a nucleophile 22 in the presence of copper as a catalyst by using the Ullmann reaction well known in the art. Finally compounds of formula 23 can be formed by displacement with an excess of the nucleophile 22 under microwave irradiations at high temperature. These reactions are amenable to a variety of substituted nucleophiles 22.

Scheme VII

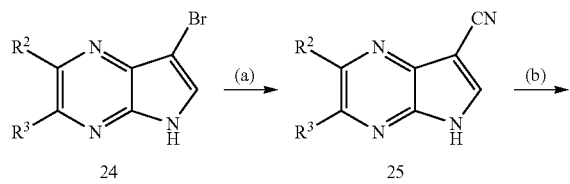

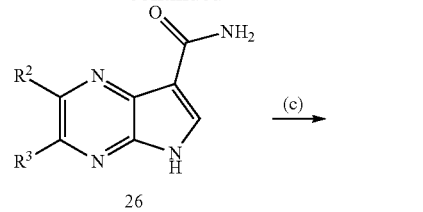

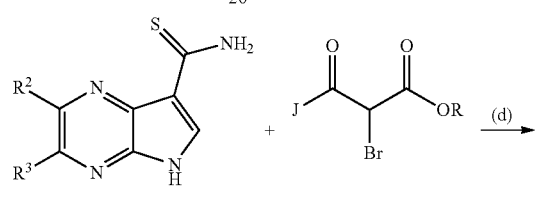

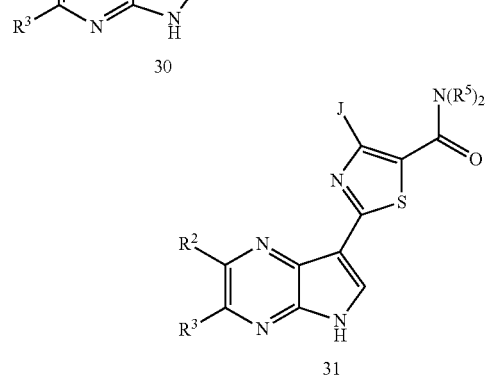

Reagents and conditions:
(a) CuCN, DMF, 80° C., 18 hours;
(b) KOH, EtOH, 30% H₂O₂, 55-60° C., 1 hour;
(c) Lawesson's reagent, Toluene, 110° C., O/N;
(d) EtOH, reflux, O/N;
(e) EtOH, 1 N NaOH, 12 hours;
(f) EDC, HOBt, DMF, N(R⁵)₂H, RT, O/N.

Scheme VII above shows a general synthetic route that is used for preparing the compounds 31 of this invention when $R^2$, $R^3$, R, $R^5$ and J are as described herein. Intermediates 25, prepared by reaction of the bromo analogues 24 with copper cyanide, are partially hydrolysed to derivatives 26 in presence of alkaline peroxide. Derivatives 27 are formed by reaction of compounds 26 with Lawesson's reagent. The cyclisation of compounds 27 in presence of β-ketoesters 28 afford intermediates 29. The reaction is amenable to a variety of β-ketoesters 28. After saponification of the esters 29, derivatives 31 are formed by a coupling reaction step well known to one of skill in the art.

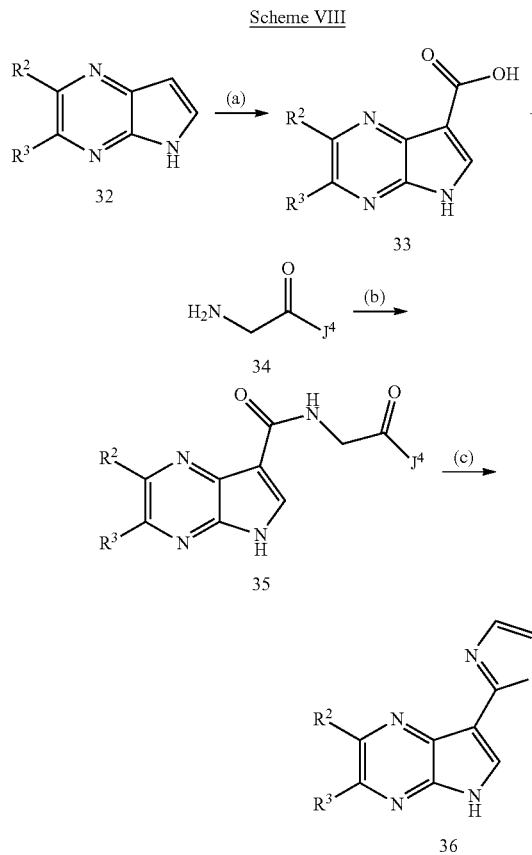

Scheme VIII

Reagents and conditions:
(a) i) DMF, POCl$_3$, 1 hour;
   ii) oxidation
(b) CDI, DMF;
(c) P$_2$S$_5$, pyridine.

Scheme VIII above shows a general synthetic route that is used for preparing the compounds 36 of this invention when R$^2$ and R$^3$ are as described herein. J$^4$ corresponds to J as defined herein. Intermediates 33 are prepared by a Vilsmeier-Haack reaction of derivatives 32 followed by an oxidation towards the acids 33. Intermediates 33 react with amines 34 following Scheme VII step (b). The reaction is amenable to a variety of amines 34. The cyclisation of compounds 35 in presence of P$_2$S$_5$ affords the desired derivatives 36.

Table II below depicts data for certain exemplary compounds. Compound numbers correspond to those compounds depicted in Table 1. $^1$H-NMR spectra was recorded at 400 MHz using a Bruker DPX 400 instrument. As used herein, the term "Rt(min)" refers to the HPLC retention time, in minutes, associated with the compound. Unless otherwise indicated, the HPLC method utilized to obtain the reported retention time is as follows:
Column: ACE C8 column, 4.6×150 mm
Gradient: 0-100% acetonitrile+methanol 60:40 (20 mM Tris phosphate)
Flow rate: 1.5 mL/minute
Detection: 225 nm.

Mass spec. samples were analyzed on a MicroMass Quattro Micro mass spectrometer operated in single MS mode with electrospray ionization.

TABLE II

| Compound No. | M + 1 (obs) | 1H NMR | Rt (mins) |
|---|---|---|---|
| I-1 | 310, 312 | (DMSO-d6): 7.35-7.45 (2H, m), 8.10-8.15 (1H, d), 8.35 (1H, s), 8.4 (1H, s), 8.6 (1H, s) | 10.3 |
| I-2 | 360, 362 | (MeOH-d4): 2.95-3.00 (6H, s), 3.50-3.55 (2H, m), 3.80-3.90 (2H, m), 7.30-7.40 (2H, m), 7.80-7.85 (1H, s), 7.90-8.00 (2H, m), 8.40-8.50 (1H, s) | 10.2 |
| I-28 | — | (MeOH-d4): 1.70-1.80 (3H, d), 5.75-5.85 (1H, qd), 7.05-7.15 (2H, t), 7.50-7.60 (2H, m), 8.40 (1H, d), 8.50 (1H, s), 8.80 (1H, s) | 9.4 |
| I-81 | 354.5 | 7.36-7.49 (2H, m), 8.11-8.20 (1H, m), 8.30-8.49 (2H, m), 8.61-8.69 (1H, m), 12.75 (1H, br s) | 10.39 |
| I-82 | 359.7 | 3.48-3.60 (4H, m), 3.76-3.89 (4H, m), 7.30-7.38 (2H, m), 8.11 (1H, s), 8.17-8.30 (2H, m), 8.48 (1H, br s), 12.01 (1H, br s) | 9.83 |
| I-83 | 274.6 | 7.21-7.30 (1H, m), 7.40-7.49 (2H, m), 8.10-8.15 (1H, m), 8.44 (1H, s), 8.53 (1H, s), 12.64 (1H, br s) | 9.67 |
| I-84 | 252.6 | 7.10 (1H, brs), 7.26 (1H, brs), 7.75 (1H, brs), 7.83 (1H, brs), 8.70 (1H, s), 12.10 (1H, brs) | 9.04 |

5. Uses, Formulation and Administration

As discussed above, the present invention provides compounds that are inhibitors of protein kinases, and thus the present compounds are useful for the treatment of diseases, disorders, and conditions including, but not limited to an autoimmune, inflammatory, proliferative, or hyperproliferative disease or an immunologically-mediated disease. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

One aspect of this invention relates to a method for treating a disease state in patients that is alleviated by treatment with a protein kinase inhibitor, which method comprises administering to a patient in need of such a treatment a therapeutically effective amount of a compound of formula I.

Another aspect of this invention relates to a method of treating or lessening the severity of a disease or condition selected from a proliferative disorder, a cardiac disorder, a neurodegenerative disorder, an autoimmune disorder, a condition associated with organ transplant, an inflammatory disorder, an immunologically mediated disorder, a viral disease, or a bone disorder in a patient, comprising the step of administering to said patient a compound or composition of this invention.

In one embodiment, the method is particularly useful for treating a disease state that is alleviated by the use of an inhibitor of aurora or aurora A.

In certain embodiments of the present invention an "effective amount" of the compound or pharmaceutically acceptable composition is that amount effective for an aurora or aurora A mediated disease. The compounds and compositions, according to the method of the present invention, may be administered using any amount and any route of administration effective for treating or lessening the severity of an aurora or aurora A mediated disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. In certain embodiments, the compound is in an amount to detectably inhibit Aurora protein kinase activity.

The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The activity of the compounds as protein kinase inhibitors, for example as aurora A inhibitors, may be assayed in vitro, in vivo or in a cell line. In vitro assays include assays that determine inhibition of either the kinase activity or ATPase activity of activated aurora A. Alternate in vitro assays quantitate the ability of the inhibitor to bind to aurora A and may be measured either by radiolabelling the inhibitor prior to binding, isolating the inhibitor/aurora A complex and determining the amount of radiolabel bound, or by running a competition experiment where new inhibitors are incubated with aurora A protein kinase bound to known radioligands.

According to one embodiment, these pharmaceutical compositions comprise a compound of this invention and a pharmaceutically acceptable carrier. According to one embodiment, these pharmaceutical compositions comprise an amount of the protein inhibitor effective to treat or prevent an aurora or aurora A mediated condition and a pharmaceutically acceptable carrier.

The term "protein kinase-mediated condition", as used herein means any disease or other deleterious condition in which a protein kinase is known to play a role. Such conditions include, without limitation, autoimmune diseases, inflammatory diseases, neurological and neurodegenerative diseases, cancer, cardiovascular diseases, allergy and asthma. The term "cancer" includes, but is not limited to the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon, adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum; brain and central nervous system; and leukemia.

The term "aurora-mediated condition", as used herein means any disease or other deleterious condition in which aurora, in particular aurora A, is known to play a role. Such conditions include, without limitation, cancer such as colon and breast cancer.

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of an aurora protein kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange.

Further examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4} alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Additional examples include sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally, intracisternally, intraperitoneally, or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal or vaginal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of aurora kinase protein kinase inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing an aurora-mediated condition comprising the step of administering to a patient one of the above-described pharmaceutical compositions.

In one embodiment, that method is used to treat or prevent a condition selected from cancers such as cancers of the breast, colon, prostate, skin, pancreas, brain, genitourinary tract, lymphatic system, stomach, larynx and lung, including lung adenocarcinoma and small cell lung cancer; stroke, diabetes, myeloma, hepatomegaly, cardiomegaly, Alzheimer's disease, cystic fibrosis, and viral disease, or any specific disease or disorder described above.

In certain embodiments, the methods according to this invention comprise the additional step of administering to said patient an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating destructive bone disorders, an agent for treating liver disease, an anti-viral agent, an agent for treating blood disorders, an agent for treating diabetes, or an agent for treating immunodeficiency disorders, wherein: 1) said additional therapeutic agent is appropriate for the disease being treated; and 2) said additional therapeutic agent is administered together with said composition as a single dosage form or separately from said composition as part of a multiple dosage form.

Those additional agents may be administered separately, as part of a multiple dosage regimen, from the aurora inhibitor-containing composition. Alternatively, those agents may be part of a single dosage form, mixed together with the aurora inhibitor in a single composition.

6. Biological Methods

EXAMPLE 1

Aurora A Inhibition Assay

Compounds were screened for their ability to inhibit full length Aurora-A (AA 1-403) activity using a standard coupled enzyme system (Fox et al., *Protein Sci.,* 7, pp. 2249 (1998)). Reactions were carried out in a solution containing 100 mM HEPES (pH 7.5), 10 mM $MgCl_2$, 25 mM NaCl, 300 µM NADH, 1 mM DTT and 3% DMSO. Final substrate concentrations in the assay were 200 µM ATP (Sigma Chemicals, St Louis, Mo.) and 800 µM peptide (LRRASLG, American Peptide, Sunnyvale, Calif.). Reactions were carried out at 30° C. and 35 nM Aurora-A. Final concentrations of the components of the coupled enzyme system were 2.5 mM phosphoenolpyruvate, 200 µM NADH, 60 µg/ml pyruvate kinase and 20 µg/ml lactate dehydrogenase.

An assay stock buffer solution was prepared containing all of the reagents listed above with the exception of ATP and the test compound of interest. The assay stock buffer solution (60 µl) was incubated in a 96 well plate with 2 µl of the test compound of interest at final concentrations spanning 0.002 µM to 30 µM at 30° C. for 10 min. Typically, a 12 point titration was conducted by preparing serial dilutions (from 1 mM compound stocks) with DMSO of the test compounds in daughter plates. The reaction was initiated by the addition of 5 µl of ATP (final concentration 200 µM). Rates of reaction were obtained using a Molecular Devices Spectramax plate reader (Sunnyvale, Calif.) over 10 min at 30° C. The Ki values were determined from the rate data as a function of inhibitor concentration using computerized nonlinear regression (Prism 3.0, Graphpad Software, San Diego, Calif.). Compounds were tested and found to inhibit Aurora A. Compounds I-1 and I-28 were tested and found to inhibit Aurora A with a Ki of less than 200 nM.

EXAMPLE 2

Aurora B Inhibition Assay (Radiometric)

An assay buffer solution is prepared which consists of 25 mM HEPES (pH 7.5), 10 mM $MgCl_2$, 0.1% BSA and 10% glycerol. A 22 nM Aurora-B solution, also containing 1.7 mM DTT and 1.5 mM Kemptide (LRRASLG), is prepared in assay buffer. To 22 µL of the Aurora-B solution, in a 96-well plate, is added 2 µl of a compound stock solution in DMSO and the mixture is allowed to equilibrate for 10 minutes at 25° C. The enzyme reaction is initiated by the addition of 16 µl stock [□-$^{33}$P]-ATP solution (~20 nCi/µL) prepared in assay buffer, to a final assay concentration of 800 µM. The reaction is stopped after 3 hours by the addition of 16 µL 500 mM phosphoric acid and the levels of $^{33}$P incorporation into the peptide substrate is determined by the following method.

A phosphocellulose 96-well plate (Millipore, Cat no. MAPHNOB50) is pre-treated with 100 µL of a 100 mM phosphoric acid prior to the addition of the enzyme reaction mixture (40 µL). The solution is left to soak on to the phosphocellulose membrane for 30 minutes and the plate subsequently is washed four times with 200 µL of a 100 mM phosphoric acid. To each well of the dry plate is added 30 µL of Optiphase 'SuperMix' liquid scintillation cocktail (Perkin Elmer) prior to scintillation counting (1450 Microbeta Liquid Scintillation Counter, Wallac). Levels of non-enzyme catalysed background radioactivity are determined by adding 16 µl of the 500 mM phosphoric acid to control wells, containing all assay components (which acts to denature the enzyme), prior to the addition of the [☐-$^{33}$P]-ATP solution. Levels of enzyme catalysed $^{33}$P incorporation are calculated by subtracting mean background counts from those measured at each inhibitor concentration. For each Ki determination 8 data points, typically covering the concentration range 0-10 µM compound, are obtained in duplicate (DMSO stocks are prepared from an initial compound stock of 10 mM with subsequent 1:2.5 serial dilutions). Ki values are calculated from initial rate data by non-linear regression using the Prism software package (Prism 3.0, Graphpad Software, San Diego, Calif.).

We claim:

1. A method of inhibiting Aurora protein kinase activity in a patient comprising administering to said patient a compound selected from a compound of formula I:

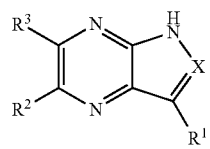

or a pharmaceutically acceptable salt thereof,
wherein X is CH;
$R^1$ is a 2-pyridyl ring independently and optionally substituted with up to five J groups;
$R^2$ and $R^3$ are each independently hydrogen, halogen, CN, $NO_2$ or V—$R^a$ optionally substituted with $R^7$;
$R^4$ is $R^5$, $C_{1-4}$aralkyl, —$COR^5$, —$CO_2R^5$, $CON(R^5)_2$, $SO_2R^5$, or $SO_2N(R^5)_2$; or two $R^4$ taken together with the atom(s) to which they are attached form an optionally substituted 3-10 membered cycloaliphatic or 5-6 membered heterocyclyl;
$R^5$ is R, $C_{6-10}$ aryl, $C_{3-10}$ cycloaliphatic, 5-6 membered heteroaryl, or 5-6 membered heterocyclyl; or two $R^5$ groups, together with the atom(s) to which they are attached, form an optionally substituted 3-7 membered monocyclic or 8-14 membered bicyclic ring;
R is H or optionally substituted $C_{1-6}$ aliphatic;
$R^a$ is optionally substituted $C_{6-10}$ aryl, $C_{3-10}$ cycloaliphatic, 5-6 membered heteroaryl, or 5-6 membered heterocyclyl;
V is a bond;
each J is independently halogen, optionally substituted $C_{1-6}$aliphatic, $C_{1-6}$ alkoxy, —$N(R^5)_2$, —$C(O)R^5$, —$NC(O)R^5$, —$C(O)NR^5$, —$C(O)OR^5$, $SOR^5$, —$SO_2R^5$, or —U—$(R^6)_n$ wherein
  each $R^6$ is independently H or optionally substituted $C_{1-12}$ aliphatic, $C_{3-10}$ cycloaliphatic, $C_{7-12}$-benzofused cycloaliphatic, $C_{6-10}$aryl, 5-6 membered heterocyclyl, 5-6 membered heteroaryl, $OR^5$, $N(R^4)_2$, or $SR^5$;
  U is a bond or optionally substituted $C_{1-6}$ aliphatic wherein up to two methylene units are optionally and independently replaced by Y in a chemically stable arrangement;
  Y is a group selected from —O—, —$NR^5$—, —S—, —$NR^5C(O)$—, —$N(SO_2)$—, —$NR^5C(O)NR^5$—, —$C(O)NR^5$—, —$C(O)$—, —$OC(O)NR^5$—, —$NR^5C(O)O$—, —$C(O)O$—, or —$OC(O)$—;
n is 1 or 2;
$R^7$ is =O, =$NR^5$, =S, —CN, —$NO_2$, or Z—$R^c$;
Z is a bond or optionally substituted $C_{1-6}$ aliphatic wherein up to two methylene units of the chain are optionally and independently replaced by —$NR^5$—, —S—, —O—, —CS—, —C(O)O—, —OC(O)—, —C(O)—, —C(O)C(O)—, —$C(O)NR^5$—, —$NR^5C(O)$—, —$NR^5C(O)O$—, —$SO_2NR^5$—, —$NR^5SO_2$—, —$C(O)NR^5NR^5$—, —$NR^5C(O)NR^5$—, —$OC(O)NR^5$—, —$NR^5NR^5$—, —$NR^5SO_2NR^5$—, —SO—, —$SO_2$—, —PO—, —$PO_2$—, or —$POR^5$—;
$R^c$ is an optionally substituted 3-8-membered saturated, partially unsaturated, or fully unsaturated monocyclic ring having 0-3 heteroatoms independently selected from nitrogen, oxygen, or sulfur, or an optionally substituted 8-12 membered saturated, partially unsaturated, or fully unsaturated bicyclic ring system having 0-5 heteroatoms independently selected from nitrogen, oxygen, or sulfur;
provided that
  when one of $R^2$ or $R^3$ is optionally substituted phenyl, the other one of $R^2$ or $R^3$ is not

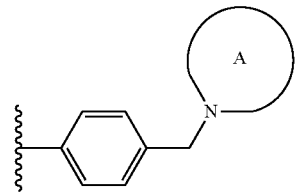

wherein ring A is an optionally substituted heterocyclyl;
optional substituents on the unsaturated carbon atom of an aryl or heteroaryl group are generally selected from halogen; —$R^o$; —$OR^o$; —$SR^o$; phenyl (Ph) optionally substituted with $R^o$; —O(Ph) optionally substituted with $R^o$; —$(CH_2)_{1-2}$(Ph), optionally substituted with $R^o$; —CH=CH(Ph), optionally substituted with $R^o$; a 5-6 membered heteroaryl or heterocyclic ring optionally substituted with $R^o$; —$NO_2$; —CN; —$N(R^o)_2$; —$NR^oC(O)R^o$; —$NR^oC(S)R^o$; —$NR^oC(O)N(R^o)_2$; —$NR^oC(S)N(R^o)_2$; —$NR^oCO_2R^o$; —$NR^oNR^oC(O)R^o$; —$NR^oNR^oC(O)N(R^o)_2$; —$NR^oNR^oCO_2R^o$; —C(O)C(O)$R^o$; —C(O)$CH_2C(O)R^o$; —$CO_2R^o$; —C(O)$R^o$; —C(S)$R^o$; —C(O)$N(R^o)_2$; —C(S)$N(R^o)_2$; —OC(O)$N(R^o)_2$; —OC(O)$R^o$; —C(O)N(O$R^o$)$R^o$; —C(NO$R^o$)$R^o$; —S(O)$_2R^o$; —S(O)$_3R^o$; —$SO_2N(R^o)_2$; —S(O)$R^o$; —$NR^oSO_2N(R^o)_2$; —$NR^oSO_2R^o$; —N(OR$^o$)$R^o$; —C(=NH)—N($R^o$)$_2$; —P(O)$_2R^o$; —PO($R^o$)$_2$; —OPO($R^o$)$_2$; or —$(CH_2)_{0-2}$NHC(O)$R^o$; wherein each independent occurrence of $R^o$ is selected from hydrogen, optionally substituted $C_{1-6}$ aliphatic, an unsubstituted 5-6 membered heteroaryl or heterocyclic ring, phenyl, —O(Ph), or —$CH_2$(Ph), or, notwithstanding the definition above, two independent occurrences of $R^o$, on the same substituent or different substituents, taken together with the atom(s) to which each $R^o$ group is bound, to form an optionally substituted 3-12 membered saturated, partially unsaturated, or fully unsaturated monocyclic or bicyclic ring having 0-4 heteroatoms independently selected from nitrogen, oxygen, or sulfur;

optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R° is unsubstituted;

optional substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic group;

optional substituents on the nitrogen of a non-aromatic heterocyclic ring are generally selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^{+1}$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form an optionally substituted 3-12 membered saturated, partially unsaturated, or fully unsaturated monocyclic or bicyclic ring having 0-4 heteroatoms independently selected from nitrogen, oxygen, or sulfur;

optional substituents on the aliphatic group or the phenyl ring of R$^+$ are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —CO$_2$H, —CO$_2$(C$_{1-4}$ aliphatic), —O(halo C$_{1-4}$ aliphatic), or halo(C$_{1-4}$ aliphatic), wherein each of the foregoing C$_{1-4}$aliphatic groups of R$^+$ is unsubstituted.

2. A method of inhibiting Aurora protein kinase activity in a patient comprising administering to said patient a compound of claim 1 selected from the following compounds:

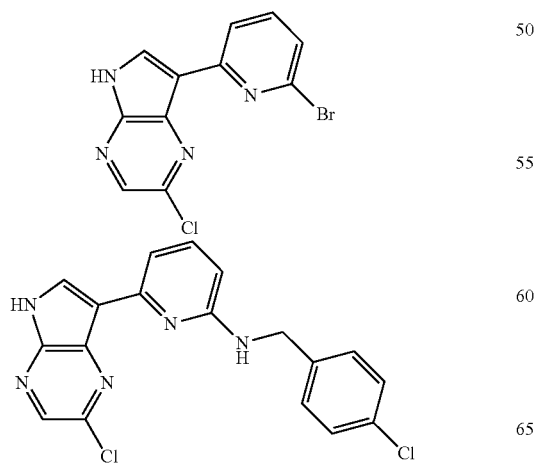

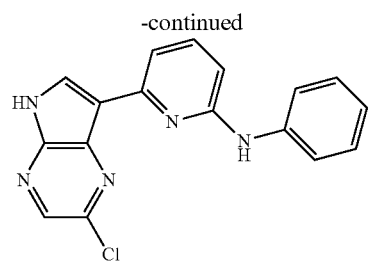

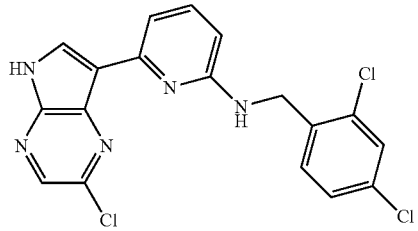

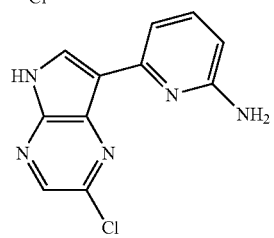

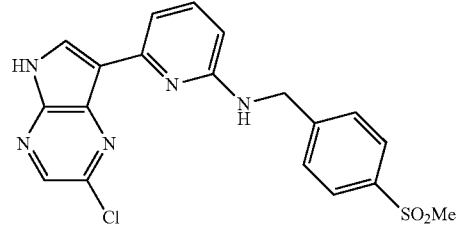

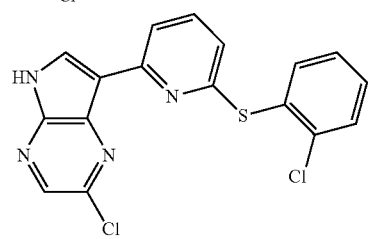

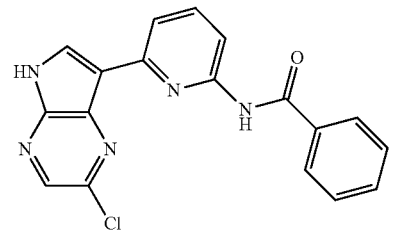

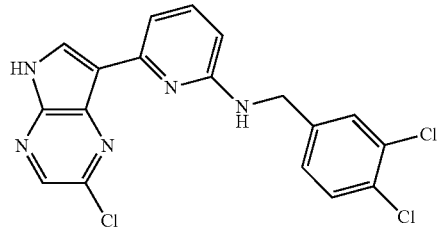

47
-continued
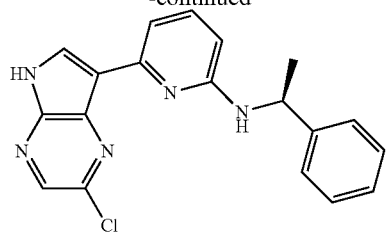
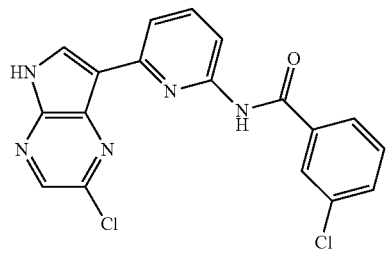
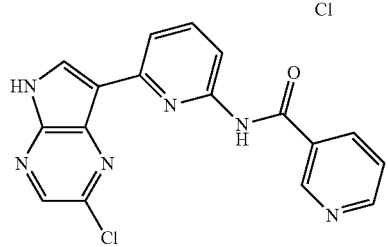
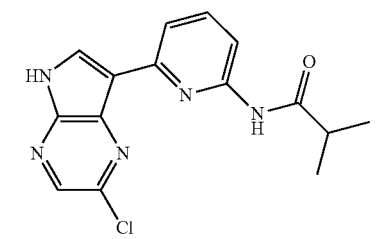
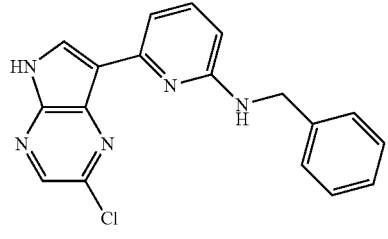
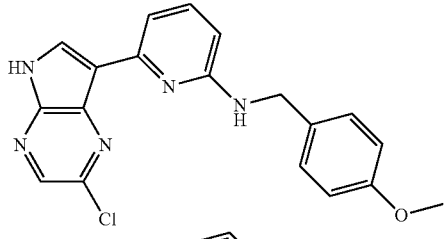
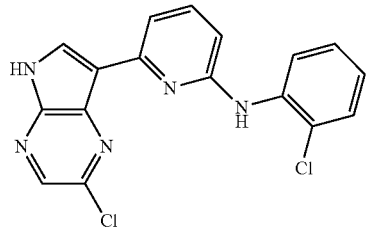
48
-continued
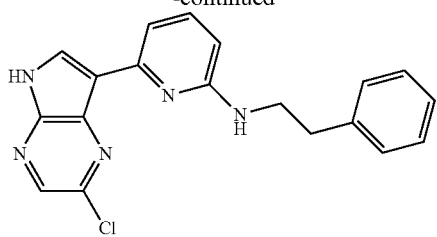
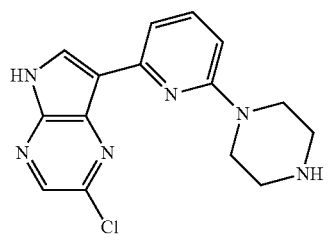
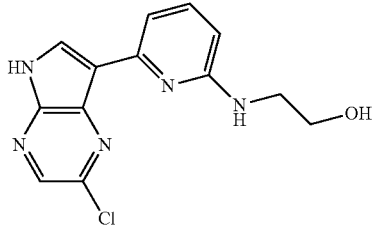
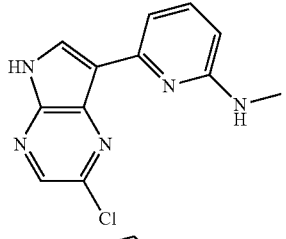
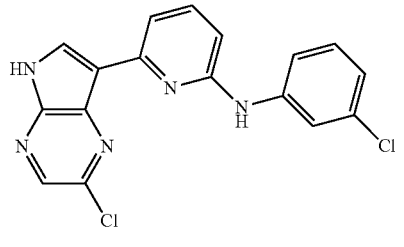
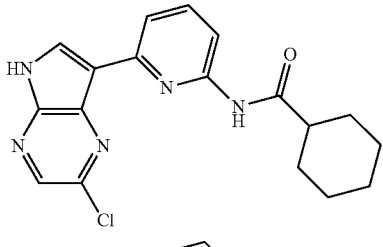
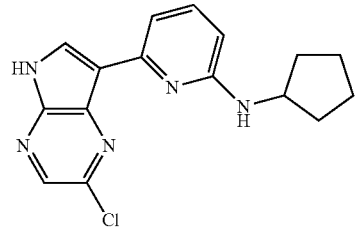

-continued
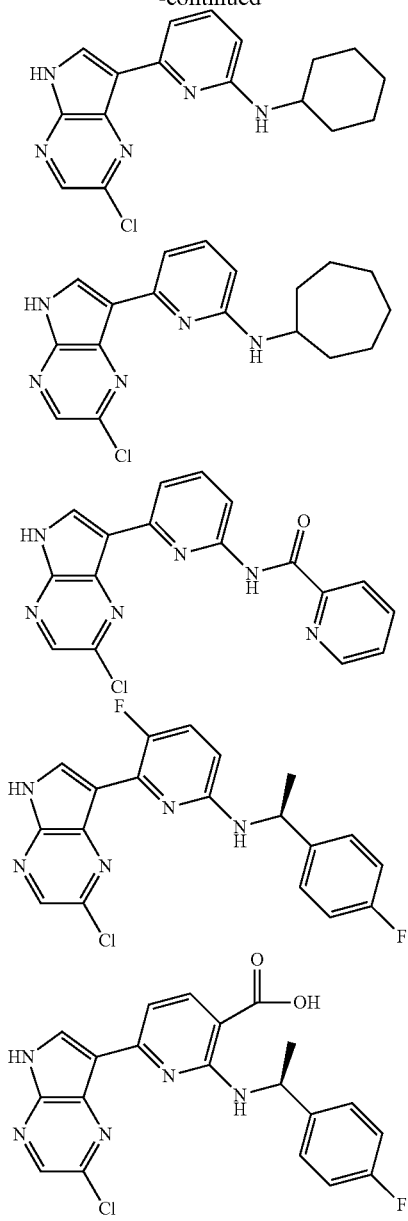
-continued
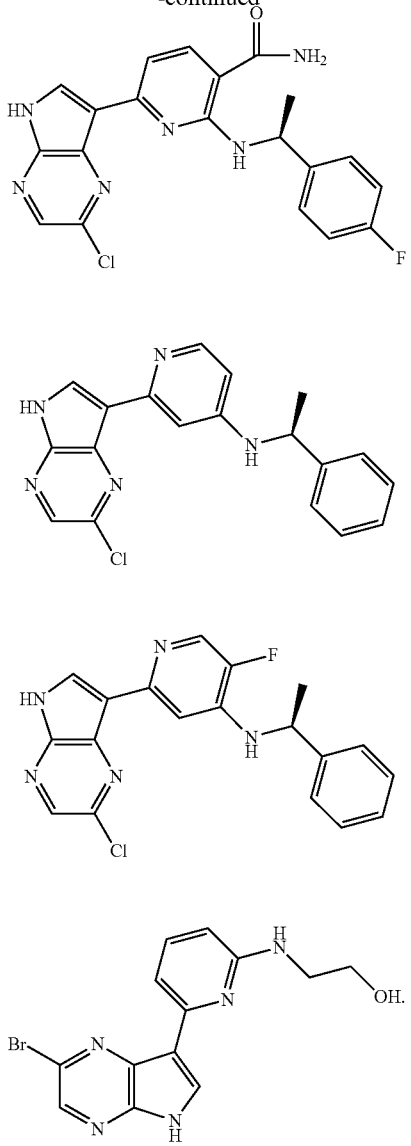
* * * * *